(12) United States Patent
Bojarski et al.

(10) Patent No.: US 8,500,740 B2
(45) Date of Patent: Aug. 6, 2013

(54) PATIENT-SPECIFIC JOINT ARTHROPLASTY DEVICES FOR LIGAMENT REPAIR

(75) Inventors: Ray Bojarski, Lexington, MA (US);
Philipp Lang, Lexington, MA (US);
Daniel Steines, Lexington, MA (US);
Wolfgang Fitz, Sherborn, MA (US)

(73) Assignee: ConforMIS, Inc., Bedford, MA (US)

( * ) Notice: Subject to any disclaimer, the term of this patent is extended or adjusted under 35 U.S.C. 154(b) by 152 days.

(21) Appl. No.: 12/761,865

(22) Filed: Apr. 16, 2010

(65) Prior Publication Data
US 2010/0298894 A1 Nov. 25, 2010

Related U.S. Application Data

(63) Continuation-in-part of application No. 11/671,745, filed on Feb. 6, 2007, now Pat. No. 8,066,708.

(60) Provisional application No. 61/169,823, filed on Apr. 16, 2009, provisional application No. 60/765,592, filed on Feb. 6, 2006, provisional application No. 60/785,168, filed on Mar. 23, 2006, provisional application No. 60/788,339, filed on Mar. 31, 2006.

(51) Int. Cl.
*A61B 17/56* (2006.01)

(52) U.S. Cl.
USPC .................... 606/86 R; 606/87; 606/88

(58) Field of Classification Search
USPC ............ 606/86 R, 88, 87, 84, 80, 79, 89, 606/96; 128/898; 623/20.35, 901
See application file for complete search history.

(56) References Cited

U.S. PATENT DOCUMENTS

| | | | |
|---|---|---|---|
| 3,314,420 A | 4/1967 | Smith et al. | 128/92 |
| 3,605,123 A | 9/1971 | Hahn | 3/1 |
| 3,798,679 A | 3/1974 | Ewald | 3/1 |
| 3,808,606 A | 5/1974 | Tronzo | 3/1 |
| 3,843,975 A | 10/1974 | Tronzo | 3/1 |
| 3,855,638 A | 12/1974 | Pilliar | 3/1 |
| 3,938,198 A | 2/1976 | Kahn et al. | 3/1.912 |
| 3,987,499 A | 10/1976 | Scharbach et al. | 3/1.91 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,098,626 A | 7/1978 | Graham et al. | 149/19.4 |

(Continued)

FOREIGN PATENT DOCUMENTS

| | | |
|---|---|---|
| DE | 2306552 | 8/1974 |
| DE | 3516743 | 11/1986 |

(Continued)

OTHER PUBLICATIONS

Andersson et al., "MacIntosh Arthroplasty In Rheumatoid Arthritis," Acta. Orthrop. Scand. 45(2):245-259 (1974).

(Continued)

*Primary Examiner* — Pedro Philogene
(74) *Attorney, Agent, or Firm* — Sunstein Kann Murphy & Timbers LLP

(57) ABSTRACT

Disclosed herein are methods, compositions and tools for repairing, replacing or otherwise treating bone ligaments using devices designed from patient-specific information, including without limitation, surgical alignment instruments that have a surface that conforms to at least a portion of a patient's bone, cartilage or other component of the joint or ligament being treated.

20 Claims, 15 Drawing Sheets

U.S. PATENT DOCUMENTS

| | | | |
|---|---|---|---|
| 4,203,444 A | 5/1980 | Bonnell et al. | 128/276 |
| 4,213,816 A | 7/1980 | Morris | 156/245 |
| 4,340,978 A | 7/1982 | Buechel et al. | 3/1.911 |
| 4,368,040 A | 1/1983 | Weissman | 433/36 |
| 4,436,684 A | 3/1984 | White | 264/138 |
| 4,501,266 A | 2/1985 | McDaniel | 128/69 |
| 4,502,161 A | 3/1985 | Wall | 3/1.91 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,715,860 A | 12/1987 | Amstutz et al. | 623/22 |
| 4,721,104 A | 1/1988 | Kaufman et al. | 128/92 |
| 4,759,350 A | 7/1988 | Dunn et al. | 128/92 VW |
| 4,769,040 A | 9/1988 | Wevers | 623/20 |
| 4,841,975 A | 6/1989 | Woolson | 128/653 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 4,936,862 A | 6/1990 | Walker et al. | 623/23 |
| 4,979,949 A * | 12/1990 | Matsen et al. | 606/53 |
| 5,041,138 A | 8/1991 | Vacanti et al. | 623/16 |
| 5,053,039 A | 10/1991 | Hofmann et al. | 606/87 |
| 5,059,216 A | 10/1991 | Winters | 623/20 |
| 5,067,964 A | 11/1991 | Richmond et al. | 623/18 |
| 5,122,144 A | 6/1992 | Bert et al. | 606/88 |
| 5,129,908 A | 7/1992 | Petersen | 606/88 |
| 5,133,759 A | 7/1992 | Turner | 623/20 |
| 5,154,717 A | 10/1992 | Matsen, III et al. | 606/53 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,250,050 A | 10/1993 | Poggie et al. | 606/79 |
| 5,258,032 A | 11/1993 | Bertin | 623/20 |
| 5,270,300 A | 12/1993 | Hunziker | 514/12 |
| 5,288,797 A | 2/1994 | Khalil et al. | 524/872 |
| 5,303,148 A | 4/1994 | Mattson et al. | 364/413.01 |
| 5,306,311 A | 4/1994 | Stone et al. | 623/18 |
| 5,314,482 A | 5/1994 | Goodfellow et al. | 623/20 |
| 5,344,459 A | 9/1994 | Swartz | 623/18 |
| 5,360,446 A | 11/1994 | Kennedy | 623/16 |
| 5,368,858 A | 11/1994 | Hunziker | 424/423 |
| 5,380,332 A | 1/1995 | Ferrante | 606/79 |
| 5,387,216 A | 2/1995 | Thornhill et al. | 606/88 |
| 5,437,676 A | 8/1995 | Bouraly et al. | 606/88 |
| 5,468,787 A | 11/1995 | Braden et al. | 523/113 |
| 5,474,559 A | 12/1995 | Bertin et al. | 606/89 |
| 5,478,739 A | 12/1995 | Slivka et al. | 435/240.23 |
| 5,486,180 A | 1/1996 | Dietz et al. | 606/87 |
| 5,501,687 A | 3/1996 | Willert et al. | 606/94 |
| 5,503,162 A | 4/1996 | Athanasiou et al. | 128/774 |
| 5,523,843 A | 6/1996 | Yamane et al. | 356/363 |
| 5,540,696 A | 7/1996 | Booth, Jr. et al. | 606/88 |
| 5,542,947 A | 8/1996 | Treacy | 606/88 |
| 5,554,190 A | 9/1996 | Draenert | 623/16 |
| 5,556,432 A | 9/1996 | Kubein-Meesenburg et al. | 623/20 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,593,450 A | 1/1997 | Scott et al. | 623/20 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,632,745 A | 5/1997 | Schwartz | 606/75 |
| 5,649,929 A | 7/1997 | Callaway | 606/88 |
| 5,658,291 A | 8/1997 | Techiera | 606/80 |
| 5,671,741 A | 9/1997 | Lang et al. | 128/653.2 |
| 5,681,316 A | 10/1997 | DeOrio et al. | 606/88 |
| 5,682,886 A | 11/1997 | Delp et al. | 128/653.1 |
| 5,683,466 A | 11/1997 | Vitale | 623/18 |
| 5,684,562 A | 11/1997 | Fujieda | 351/212 |
| 5,688,282 A | 11/1997 | Baron et al. | 606/90 |
| 5,690,635 A * | 11/1997 | Matsen et al. | 606/88 |
| 5,728,162 A | 3/1998 | Eckhoff | 623/20 |
| 5,735,277 A | 4/1998 | Schuster | 128/653.1 |
| 5,749,874 A | 5/1998 | Schwartz | 606/75 |
| 5,749,876 A | 5/1998 | Duvillier et al. | 606/88 |
| 5,768,134 A | 6/1998 | Swaelens et al. | 364/468.28 |
| 5,769,899 A | 6/1998 | Schwartz et al. | 623/18 |
| 5,776,137 A | 7/1998 | Katz | 606/88 |
| 5,786,217 A | 7/1998 | Tubo et al. | 435/402 |
| 5,800,438 A | 9/1998 | Tuke et al. | 606/90 |
| 5,827,289 A | 10/1998 | Reiley et al. | 606/86 |
| 5,830,216 A | 11/1998 | Insall et al. | 606/88 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,860,981 A | 1/1999 | Bertin et al. | 606/89 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,298 A * | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,911,723 A | 6/1999 | Ashby et al. | 606/88 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,001,895 A | 12/1999 | Harvey et al. | 523/113 |
| 6,002,859 A | 12/1999 | DiGioia, III et al. | 395/500.32 |
| 6,007,537 A | 12/1999 | Burkinshaw et al. | 606/66 |
| 6,010,509 A | 1/2000 | Delgado et al. | 606/88 |
| 6,013,103 A | 1/2000 | Kaufman et al. | 623/20 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,057,927 A | 5/2000 | Lévesque et al. | 356/432 T |
| 6,077,270 A | 6/2000 | Katz | 606/88 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,096,043 A | 8/2000 | Techiera et al. | 606/88 |
| 6,102,916 A | 8/2000 | Masini | 606/86 |
| 6,106,529 A | 8/2000 | Techiera | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |
| 6,156,069 A | 12/2000 | Amstutz | 623/22.11 |
| 6,161,080 A | 12/2000 | Aouni-Ateshian et al. | 703/11 |
| 6,187,010 B1 | 2/2001 | Masini | 606/86 |
| 6,200,606 B1 | 3/2001 | Peterson et al. | 424/574 |
| 6,203,546 B1 | 3/2001 | MacMahon | 606/87 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,251,143 B1 | 6/2001 | Schwartz et al. | 623/23.72 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,296,646 B1 | 10/2001 | Williamson | 606/90 |
| 6,299,905 B1 | 10/2001 | Peterson et al. | 424/486 |
| 6,322,588 B1 | 11/2001 | Ogle et al. | 623/1.46 |

| Patent/Publication | Date | Inventor | Class |
|---|---|---|---|
| 6,328,765 B1 | 12/2001 | Hardwick et al. | 623/23.72 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,459,948 B1 | 10/2002 | Ateshian et al. | 700/117 |
| 6,468,314 B2 | 10/2002 | Schwartz et al. | 623/23.72 |
| 6,478,799 B1 | 11/2002 | Williamson | 606/90 |
| 6,479,996 B1 | 11/2002 | Hoogeveen et al. | 324/309 |
| 6,510,334 B1 | 1/2003 | Schuster et al. | 600/407 |
| 6,520,964 B2 | 2/2003 | Tallarida et al. | 396/567 |
| 6,558,421 B1 | 5/2003 | Fell et al. | 623/14.12 |
| 6,560,476 B1 | 5/2003 | Pelletier et al. | 600/407 |
| 6,575,980 B1 | 6/2003 | Robie et al. | 606/88 |
| 6,620,168 B1 | 9/2003 | Lombardo et al. | 606/88 |
| 6,626,945 B2 | 9/2003 | Simon et al. | 623/17.19 |
| 6,626,948 B2 | 9/2003 | Storer et al. | 623/23.14 |
| 6,632,225 B2 | 10/2003 | Sanford et al. | 606/87 |
| 6,632,235 B2 | 10/2003 | Weikel et al. | 606/192 |
| 6,652,587 B2 | 11/2003 | Felt et al. | 623/20.16 |
| 6,673,077 B1 | 1/2004 | Katz | 606/88 |
| 6,679,917 B2 | 1/2004 | Ek | 623/20.14 |
| 6,712,856 B1 | 3/2004 | Carignan et al. | 623/20.35 |
| 6,905,514 B2 * | 6/2005 | Carignan et al. | 623/20.35 |
| 6,916,341 B2 | 7/2005 | Rolston | 623/20.3 |
| 6,928,742 B2 | 8/2005 | Broers et al. | 33/512 |
| 6,969,393 B2 | 11/2005 | Pinczewski et al. | 606/88 |
| 7,008,430 B2 | 3/2006 | Dong et al. | 606/80 |
| 7,060,074 B2 | 6/2006 | Rosa et al. | 606/88 |
| 7,104,997 B2 | 9/2006 | Lionberger et al. | 606/88 |
| 7,115,131 B2 | 10/2006 | Engh et al. | 606/79 |
| 7,117,027 B2 | 10/2006 | Zheng et al. | 600/426 |
| 7,141,053 B2 | 11/2006 | Rosa et al. | 606/86 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,282,054 B2 | 10/2007 | Steffensmeier et al. | 606/96 |
| 7,292,674 B2 | 11/2007 | Lang | 378/54 |
| 7,379,529 B2 | 5/2008 | Lang | 378/54 |
| 7,458,975 B2 * | 12/2008 | May et al. | 606/53 |
| 7,467,892 B2 | 12/2008 | Lang et al. | 378/207 |
| 7,468,075 B2 | 12/2008 | Lang et al. | 623/16.11 |
| 7,534,263 B2 | 5/2009 | Burdulis, Jr. et al. | 623/14.12 |
| 7,618,451 B2 | 11/2009 | Berez et al. | 623/14.12 |
| 7,747,305 B2 | 6/2010 | Dean et al. | 600/407 |
| 7,806,896 B1 | 10/2010 | Bonutti | 606/86 R |
| 7,881,768 B2 | 2/2011 | Lang et al. | 600/407 |
| 7,981,158 B2 | 7/2011 | Fitz et al. | 128/92 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,083,745 B2 | 12/2011 | Lang et al. | 606/87 |
| 8,105,330 B2 | 1/2012 | Fitz et al. | 606/88 |
| 8,112,142 B2 | 2/2012 | Alexander et al. | 600/407 |
| 8,122,582 B2 | 2/2012 | Burdulis, Jr. et al. | 29/527.1 |
| RE43,282 E | 3/2012 | Alexander et al. | 600/427 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0029038 A1 | 3/2002 | Haines | 606/54 |
| 2002/0045940 A1 | 4/2002 | Giannetti et al. | 623/11.11 |
| 2002/0059049 A1 | 5/2002 | Bradbury et al. | 703/11 |
| 2002/0068979 A1 | 6/2002 | Brown et al. | 623/20.3 |
| 2002/0079601 A1 | 6/2002 | Russell et al. | 264/40.1 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0143402 A1 | 10/2002 | Steinberg | 623/22.16 |
| 2002/0151986 A1 | 10/2002 | Asculai et al. | 424/484 |
| 2002/0173852 A1 | 11/2002 | Felt et al. | 623/20.32 |
| 2002/0183850 A1 | 12/2002 | Felt et al. | 623/20.16 |
| 2003/0028196 A1 | 2/2003 | Bonutti | 606/87 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0100907 A1 | 5/2003 | Rosa et al. | 606/86 |
| 2003/0100953 A1 | 5/2003 | Rosa et al. | 623/20.3 |
| 2003/0120347 A1 | 6/2003 | Steinberg | 623/22.17 |
| 2003/0158558 A1 | 8/2003 | Horn | 606/87 |
| 2003/0158606 A1 | 8/2003 | Coon et al. | 623/20.15 |
| 2003/0163137 A1 | 8/2003 | Smucker et al. | 606/87 |
| 2003/0173695 A1 | 9/2003 | Monkhouse et al. | 264/40.1 |
| 2003/0216669 A1 | 11/2003 | Lang et al. | 600/587 |
| 2003/0225457 A1 | 12/2003 | Justin et al. | 623/20.14 |
| 2003/0236521 A1 | 12/2003 | Brown et al. | 606/80 |
| 2004/0098133 A1 | 5/2004 | Carignan et al. | 623/20.35 |
| 2004/0102852 A1 | 5/2004 | Johnson et al. | 623/20.15 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/14.12 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167388 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0236424 A1 | 11/2004 | Berez et al. | 623/14.12 |
| 2004/0249386 A1 | 12/2004 | Faoro | 606/88 |
| 2005/0015153 A1 | 1/2005 | Goble et al. | 623/23.46 |
| 2005/0021039 A1 | 1/2005 | Cusick et al. | 606/88 |
| 2005/0043807 A1 | 2/2005 | Wood | 623/20.14 |
| 2005/0055028 A1 | 3/2005 | Haines | 606/79 |
| 2005/0085920 A1 | 4/2005 | Williamson | 623/20.14 |
| 2005/0107883 A1 | 5/2005 | Goodfried et al. | 623/20.15 |
| 2005/0107884 A1 | 5/2005 | Johnson et al. | 623/20.15 |
| 2005/0119664 A1 | 6/2005 | Carignan et al. | 606/96 |
| 2005/0143745 A1 | 6/2005 | Hodorek et al. | 606/87 |
| 2005/0148843 A1 | 7/2005 | Roose | 600/407 |
| 2005/0171545 A1 | 8/2005 | Walsh et al. | 606/72 |
| 2005/0171612 A1 | 8/2005 | Rolston | 623/20.19 |
| 2005/0192588 A1 | 9/2005 | Garcia | 606/88 |
| 2005/0234461 A1 | 10/2005 | Burdulis, Jr. et al. | 606/79 |
| 2005/0267584 A1 | 12/2005 | Burdulis et al. | 623/20.19 |
| 2006/0052795 A1 * | 3/2006 | White | 606/102 |
| 2006/0111722 A1 | 5/2006 | Bouadi | 606/79 |
| 2006/0149283 A1 | 7/2006 | May et al. | 606/96 |
| 2006/0200162 A1 | 9/2006 | Farling et al. | 606/88 |
| 2006/0235421 A1 | 10/2006 | Rosa et al. | 606/88 |
| 2007/0015995 A1 | 1/2007 | Lang | 600/407 |
| 2007/0073305 A1 | 3/2007 | Lionberger et al. | 606/87 |
| 2007/0118141 A1 | 5/2007 | Marchyn et al. | 606/88 |
| 2007/0198022 A1 | 8/2007 | Lang et al. | 606/88 |
| 2007/0203430 A1 | 8/2007 | Lang et al. | 600/587 |
| 2007/0233151 A1 * | 10/2007 | Chudik | 606/96 |
| 2007/0233156 A1 | 10/2007 | Metzger | 606/130 |
| 2007/0276224 A1 | 11/2007 | Lang et al. | 600/410 |
| 2007/0293868 A1 | 12/2007 | Delfosse et al. | 606/88 |
| 2008/0004709 A1 | 1/2008 | O'Neill et al. | 623/20.35 |
| 2008/0015433 A1 | 1/2008 | Alexander et al. | 600/427 |
| 2008/0025463 A1 | 1/2008 | Lang | 378/54 |
| 2008/0031412 A1 | 2/2008 | Lang | 378/54 |
| 2008/0058613 A1 | 3/2008 | Lang et al. | 600/300 |

| | | | | | | |
|---|---|---|---|---|---|---|
| 2008/0058945 | A1 | 3/2008 | Hajaj et al. ............... 623/20.14 | WO | WO 99/51719 | 10/1999 |
| 2008/0114370 | A1* | 5/2008 | Schoenefeld ................ 606/96 | WO | WO 99/56674 | 11/1999 |
| 2008/0170659 | A1 | 7/2008 | Lang et al. .................. 378/56 | WO | WO 00/09179 | 2/2000 |
| 2008/0195216 | A1 | 8/2008 | Philipp .................. 623/18.11 | WO | WO 00/15153 | 3/2000 |
| 2008/0219412 | A1 | 9/2008 | Lang ....................... 378/207 | WO | WO 00/35346 | 6/2000 |
| 2008/0243127 | A1 | 10/2008 | Lang et al. ................ 606/87 | WO | WO 00/48550 | 8/2000 |
| 2008/0275452 | A1 | 11/2008 | Lang et al. ................ 606/88 | WO | WO 00/59411 | 10/2000 |
| 2008/0281328 | A1 | 11/2008 | Lang et al. ................ 606/87 | WO | WO 00/74554 | 12/2000 |
| 2008/0281329 | A1 | 11/2008 | Lang et al. ................ 606/87 | WO | WO 01/10356 | 2/2001 |
| 2008/0281426 | A1 | 11/2008 | Fitz et al. ................ 623/17.16 | WO | WO 01/17463 | 3/2001 |
| 2009/0076371 | A1 | 3/2009 | Lang et al. ................ 600/407 | WO | WO 01/19254 | 3/2001 |
| 2009/0087276 | A1 | 4/2009 | Rose ........................ 409/79 | WO | WO 01/35968 | 5/2001 |
| 2009/0088753 | A1 | 4/2009 | Aram et al. ................ 606/79 | WO | WO 01/45764 | 6/2001 |
| 2009/0088758 | A1 | 4/2009 | Bennett .................... 606/82 | WO | WO 01/66021 | 9/2001 |
| 2009/0099567 | A1 | 4/2009 | Zajac ....................... 606/79 | WO | WO 01/68800 | 9/2001 |
| 2009/0131941 | A1 | 5/2009 | Park et al. ................ 606/87 | WO | WO 01/70142 | 9/2001 |
| 2009/0131942 | A1 | 5/2009 | Aker et al. ................ 606/88 | WO | WO 01/91672 | 12/2001 |
| 2009/0222014 | A1 | 9/2009 | Bojarski et al. ........... 606/88 | WO | WO 02/00270 | 1/2002 |
| 2009/0307893 | A1 | 12/2009 | Burdulis, Jr. et al. ....... 29/527.1 | WO | WO 02/00275 | 1/2002 |
| 2010/0281678 | A1 | 11/2010 | Burdulis, Jr. et al. ....... 29/592 | WO | WO 02/02158 | 1/2002 |
| 2010/0305573 | A1 | 12/2010 | Fitz et al. ................ 606/87 | WO | WO 02/22013 | 3/2002 |
| 2010/0305574 | A1 | 12/2010 | Fitz et al. ................ 606/88 | WO | WO 02/22014 | 3/2002 |
| 2011/0066193 | A1 | 3/2011 | Lang et al. ................ 606/86 R | WO | WO 02/23483 | 3/2002 |
| 2011/0071581 | A1 | 3/2011 | Lang et al. ................ 606/86 R | WO | WO 02/34310 | 5/2002 |
| | | | | WO | WO 02/36147 | 5/2002 |
| | | FOREIGN PATENT DOCUMENTS | | WO | WO 02/096268 | 12/2002 |
| | | | | WO | WO 03/007788 | 1/2003 |
| DE | | 44 34 539 | 4/1996 | WO | WO 03/37192 | 5/2003 |
| DE | | 20303498 | 8/2003 | WO | WO 03/047470 | 6/2003 |
| EP | | 0337901 | 10/1989 | WO | WO 03/051210 | 6/2003 |
| EP | | 0528080 | 2/1993 | WO | WO 03/055400 | 7/2003 |
| EP | | 0 704 193 | 4/1996 | WO | WO 2004/043305 | 5/2004 |
| EP | | 0626156 | 7/1997 | WO | WO 2004/049981 | 6/2004 |
| EP | | 0613380 | 12/1999 | WO | WO 2005/051239 | 6/2005 |
| EP | | 0993807 | 4/2000 | WO | WO 2005/051240 | 6/2005 |
| EP | | 1074229 | 2/2001 | WO | WO 2006/060795 | 6/2006 |
| EP | | 1077253 | 2/2001 | WO | WO 2006/127283 | 11/2006 |
| EP | | 1120087 | 8/2001 | WO | WO 2007/041375 | 4/2007 |
| EP | | 1129675 | 9/2001 | WO | WO 2007/092841 | 8/2007 |
| EP | | 1132061 | 9/2001 | WO | WO 2008/112996 | 9/2008 |
| EP | | 0732091 | 12/2001 | WO | WO 2008/117028 | 10/2008 |
| EP | | 0896825 | 7/2002 | WO | WO 2008/157412 | 12/2008 |
| EP | | 0814731 | 8/2002 | WO | WO 2009/111639 | 9/2009 |
| EP | | 1234552 | 8/2002 | WO | WO 2010/121147 | 10/2010 |
| EP | | 1234555 | 8/2002 | | | |
| EP | | 0809987 | 10/2002 | | OTHER PUBLICATIONS | |
| EP | | 0833620 | 10/2002 | | | |
| EP | | 0530804 | 6/2004 | | | |
| FR | | 2819714 | 7/2002 | | | |
| GB | | 1451283 | 9/1976 | | | |
| GB | | 2291355 | 1/1996 | | | |
| GB | | 2348373 | 10/2000 | | | |
| JP | | 1-249049 | 10/1989 | | | |
| JP | | 8-173465 | 7/1996 | | | |
| JP | | 9-206322 | 8/1997 | | | |
| JP | | 2002-102236 | 4/2002 | | | |
| WO | WO 87/02882 | | 5/1987 | | | |
| WO | WO 90/09769 | | 9/1990 | | | |
| WO | WO 93/04710 | | 3/1993 | | | |
| WO | WO 93/09819 | | 5/1993 | | | |
| WO | WO 93/25157 | | 12/1993 | | | |
| WO | WO 95/27450 | | 10/1995 | | | |
| WO | WO 95/28688 | | 10/1995 | | | |
| WO | WO 95/30390 | | 11/1995 | | | |
| WO | WO 95/32623 | | 12/1995 | | | |
| WO | WO 96/24302 | | 8/1996 | | | |
| WO | WO 97/25942 | | 7/1997 | | | |
| WO | WO 97/26847 | | 7/1997 | | | |
| WO | WO 97/27885 | | 8/1997 | | | |
| WO | WO 97/38676 | | 10/1997 | | | |
| WO | WO 98/12994 | | 4/1998 | | | |
| WO | WO 98/20816 | | 5/1998 | | | |
| WO | WO 98/30617 | | 7/1998 | | | |
| WO | WO 98/32384 | | 7/1998 | | | |
| WO | WO 99/02654 | | 1/1999 | | | |
| WO | WO 99/08598 | | 2/1999 | | | |
| WO | WO 99/08728 | | 2/1999 | | | |
| WO | WO 99/40864 | | 8/1999 | | | |
| WO | WO 99/42061 | | 8/1999 | | | |
| WO | WO 99/47186 | | 9/1999 | | | |

Argenson et al., "Is There a Place for Patellofemoral Arthroplasty?," Clinical Orthopaedics and Related Research No. 321, pp. 162-167 (1995).

Blum et al., "Knee Arthroplasty in Patients with Rheumatoid Arthritis," ANN. Rheum. Dis. 33 (1): 1-11 (1974).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).

Cameron, et al., "Review of a Failed Knee Replacement and Some Observations on the Design of a Knee Resurfacing Prosthesis," Arch. Orthop Trauma Surg. 97(2):87-89 (1980).

Carr et al., "Surface Interpolation with Radial Basis Functions for Medical Imaging," IEEE Transactions on Medical Imaging, IEEE, Inc. New York, vol. 16, pp. 96-107 (Feb. 1997).

Clary et al., "Experience with the MacIntosh Knee Prosthesis," South Med. J. 65(3):265-272 (1972).

Conaty, et al., "Surgery of the Hip and Knee in Patients with Rheumatoid Arthritis," J. Bone Joint Surg. Am. 55(2):301-314 (1973).

De Winter et al., "The Richards Type II Patellofemoral Arthroplasty", Acta Orthop Scand 2001; 72 (5): 487-490.

Delp et al., "A Graphics-Based Software System to Develop and Analyze Models of Musculoskeletal Structures," Comput. Biol. Med., vol. 25, No. 1, pp. 21-34, 1995.

Farrar et al., "Computed Tomography Scan Scout Film for Measurement of Femoral Axis in Knee Arthroplasty," J. Arthroplasty, vol. 14, No. 8, pp. 1030-1031, 1999.

Ghelman et al., "Kinematics of the Knee After Prosthetic Replacements", Clin. Orthop. May 1975: (108):149-157.

Hastings et al., "Double Hemiarthroplasty of the Knee in Rheumatoid Arthritis," A Survey of Fifty Consecutive Cases, J. Bone Joint Surg. Br. 55(1):112-118 (1973).

Henderson et al., "Experience with the Use of the Macintosh Prosthesis in Knees of Patients with Pheumatoid Arthritis," South. Med. J. 62(11):1311-1315 (1969).

Jessop et al., "Follow-up of the MacIntosh Arthroplasty of the Knee Joint," Rheumatol Phys. Med. 11(5):217-224 (1972).

Kates, et al., "Experiences of Arthroplasty of the Rheumatoid Knee Using MacIntosh Prostheses," Ann. Rheum. Dis. 28(3):328 (1969).

Kay et al., The MacIntosh Tibial Plateau Hemiprosthesis for the Rheumatoid Knee, J. Bone Joint Surg. Br. 54(2):256-262 (1972).

Kidder et al., "3D Model Acquisition, Design, Planning And Manufacturing Of Orthopaedic Devices: A Framework," Proceedings of the SPIE—Advanced Sensor and Control-System Interface, Boston, MA, vol. 2911, pp. 9-22, 21 (Nov. 1996).

Kim et al., "Measurement of Femoral Neck Anteversion in 3D. Part 1: 3D Imaging Method," Med. And Viol. Eng. And Computing, vol. 38, No. 6, pp. 603-609, 2000.

Kshirsagar et al., "Measurement of Localized Cartilage Volume and Thickness of Human Knee Joints by Computer Analysis of Three-Dimensional Magnetic Resonance Images", Invest Radiol. May 1998, 33(5): 289-299 T. 111, V. 111.

Lam et al., "X-Ray Diagnosis: A Physician's Approach", Editor Lam, 1998, Springer-Verlag publishers, Title page and Table of Contents pgs. Only (ISBN 9813083247).

Lam et al., "Varus/Valgus Alignment of the Femoral Component in Total Knee Arthroplasty," The Knee, vol. 10, pp. 237-241, 2003.

Leenslag et al., "A Porous Composite for Reconstruction of Meniscus Lesions," Biological and Biomechanical Perform. of Biomaterials, Elsevier Science Publishers Amsterdam pp. 147-152 (1986).

Lu et al., "In vitro degradation of porous poly(L-lactic acid) foams", Biomaterials, 21(15):1595-1605, Aug. 2000.

MacIntosh, "Arthroplasty Of The Knee In Rheumatoid Arthritis," Proceedings and Reports of Councils and Assotions, J. Bone & Joint Surg., vol. 48B No. (1): 179 (Feb. 1996).

MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).

MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).

MacIntosh, "Hemiarthroplasty of the Knee Using a Space Occupying Prosthesis for Painful Varus and Valgus Deformities," J. Bone Joint Surg. Am. Dec. 1958:40-A:1431.

Mahaisavariya et al., "Morphological Study of the Proximal Femur: A New Method of Geometrical Assessment Using 3 Dimensional Reverse Engineering," Med. Eng. And Phys., vol. 24, pp. 617-622, 2002.

Marler et al., "Soft-Tissue Augmentation with Injectable Alginate and Syngeneic Fibroblasts", Plastic & Reconstructive Surgery, 105(6):2049-2058, May 2000.

Matsen, III et al., "Robotic Assistance in Orthopaedic Surgery: A Proof of Principle Using Distal Femoral Arthroplasty", Clinical Ortho. and Related Research, 296:178-186 (1993).

McCollum et al., "Tibial Plateau Prosthesis in Arthroplasty of the Knee," J. Bone Joint Surg. Am. 1970 52(4):827-8 (Feb. 1996).

McKeever, "The Classic Tibial Plateau Prosthesis," Clin. Orthop. Relat. Res. (192):3-12 (1985).

Nelson et al., "Arthroplasty and Arthrodesis of the Knee Joint," Orthop. Clin. North Am. 2 (1): 245-64 (1971).

Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).

Porter et al., "MacIntosh Arthroplasty: A Long-Term Review," J. R. Coll. Surg. Edin. (192):199-201 (1988).

Portheine et al., "CT-Based Planning and Individual Template Navigation in TKA", Navigation and Robotics in Total Joint and Spine Surgery, Springer, 48:336-342 (2004).

Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.

Potter, "Arthroplasty of the Knee With Tibial Metallic Implants of the McKeever and MacIntosh Design," Sug. Clin. North Am. 49(4):903-915 (1969).

Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).

Radermacher, English Translation : Helmholtz Institute of Biomedical Technology, "Computer-Assisted Planning and Execution of Orthopedic Surgery Using Individual Surgical Templates", May 18, 1999.

Radermacher, German Version: Helmholtz Institute of Biomedical Technology, "Computer-Assisted Planning and Execution of Orthopedic Surgery Using Individual Surgical Templates", May 18, 1999.

Radermacher, "Computer Assisted Orthopaedic Surgery With Image Based Individual Templates" Clinical Orthopaedics, Sep. 1998, vol. 354, pp. 28-38.

Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.

Radermacher et al., "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.

Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.

Radermacher et al., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.

Ranawat et al., "MacIntosh Hemiarthroplasty in Rheumatoid Knee," Acta Orthop Belg., 39 (1): 1-11 (1973).

Schorn et al., "MacIntosh Arthroplasty in Rheumatoid Arthritis," Rheumatol Rehabil. Aug. 1978:17(3):155-163.

Slone et al., "Body CT: A Practical Approach", Editor Slone, 1999 McGraw-Hill publishers, Title page and Table of Contents pgs. Only (ISBN 007058219).

Stauffer et al., "The MacIntosh Prosthesis. Prospective Clinical and Gait Evaluation," Arch. Surg. 110(6):717-720 (1975).

Stout et al., "X-Ray Structure Determination: A Practical Guide", 2nd Ed. Editors Stout and Jensen, 1989, John Wiley & Sons, Title page and Table of Contents pgs. Only (ISBN 0471607118).

Taha et al., "Modeling And Design Of A Custom Made Cranium Implant For Large Skull Reconstruction Before A Tumor Removal", Phidias Newsletter No. 6, pp. 3, 6, Jun. 2001. Retrieved from the Internet: URL:http://www.materialise.com/medical/files/pdf.

Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.

Testi et al., "Border Tracing Algorithm Implementation for the Femoral Geometry Reconstruction," Comp. Meth. And Programs in Biomed., vol. 65, pp. 175-182, 2001.

Vandeberg et al., "Assessment of Knee Cartilage In Cadavers With Dual-Detector Spiral CT Arthrography and MR Imaging", Radiology, Feb. 2002: 222(2): 430-435.

Wiese et al., "Biomaterial properties and biocompatibility in cell culture of a novel self-inflating hydrogel tissue expander", J. Biomedical Materials Research Part A, 54(2):179-188, Nov. 2000.

Wordsworth et al., "MacIntosh Arthroplasty for the Rheumatoid Knee: A 10-year Follow Up," Ann. Rheum. Dis. 44(11):738-741 (1985).
Yusof et al., "Preparation and characterization of chitin beads as a wound dressing precursor", J. Biomedical Materials Research Part A, 54(1):59-68, Oct. 2000.
International Searching Authority, International Search Report—International Application No. PCT/US03/38158, dated Feb. 23, 2005, 6 pages.
European Patent Office, European Search Report—Application No. EP 03790194, dated Jul. 6, 2006, 5 pages.
International Searching Authority, International Search Report—International Application No. PCT/US04/39616, dated Mar. 28, 2005, together with the Written Opinion of the International Searching Authority, 6 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2006/045172, dated Apr. 19, 2007, 5 pages.
International Searching Authority, International Search Report—International Application No. PCT/US2007/061681, dated Sep. 7, 2007, together with the Written Opinion of the International Searching Authority, 12 pages.
European Patent Office, Supplementary European Search Report—Application No. 04812187.5, dated Sep. 27, 2007, 3 pages.
International Searching Authority, International Preliminary Report on Patentability—International Application No. PCT/US2005/044008, dated Jun. 14, 2007, together with the Written Opinion of the International Searching Authority, 8 pages.
International Searching Authority, International Search Report—International Application No. PCT/US2008/057045, dated Jul. 15, 2008, together with the Written Opinion of the International Searching Authority, 9 pages.
International Searching Authority, Invitation to Pay Additional Fees, and Where Applicable, Protest Fee—International Application No. PCT/US2008/066994, dated Oct. 21, 2008, 5 pages.
International Searching Authority International Search Report—International Application No. PCT/US2008/066994, dated Feb. 19, 2009, together with the Written Opinion of the International Searching Authority, 16 pages.
Bromberg & Sunstein LLP, Amendment dated Sep. 22, 2008, pertaining to U.S. Appl. No. 09/882,363, 15 pages.
United States Patent and Trademark Office, Office Action dated Jan. 6, 2009, pertaining to U.S. Appl. No. 09/882,363, 9 pages.
Bromberg & Sunstein LLP, Request for Continued Examination dated Jul. 6, 2009, pertaining to U.S. Appl. No. 09/882,363, 16 pages.
International Searching Authority, International Search Report—International Application No. PCT/US2009/036189, dated Jul. 13, 2009, together with the Written Opinion of the International Searching Authority, 11 pages.
Sunstein Kann Murphy & Timbers LLP, Supplemental Amendment dated Sep. 18, 2009, pertaining to U.S. Appl. No. 09/882,363, 11 pages.
United States Patent and Trademark Office, Office Action dated May 5, 2008, pertaining to U.S. Appl. No. 10/724,010, 13 pages.
Bromberg & Sunstein LLP, Request for Continued Examination and Response dated Nov. 4, 2008, pertaining to U.S. Appl. No. 10/724,010, 15 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office Action dated Nov. 26, 2007, pertaining to U.S. Appl. No. 11/002,573, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
United States Patent and Trademark Office, Office action dated Jan. 26, 2010, pertaining to U.S. Appl. No. 11/671,745, 9 pages.
International Searching Authority, International Search Report—International Application No. PCT/US10/31415, dated Jun. 29, 2010, together with the Written Opinion of the International Searching Authority, 9 pages.
United States Patent and Trademark Office, Office Action dated Oct. 20, 2010, pertaining to U.S. Appl. No. 12/135,719, 10 pages.
Sunstein Kann Murphy & Timbers LLP, Response to Office Action dated Aug. 26, 2010, pertaining to U.S. Appl. No. 12/361,213, 22 pages.
United States Patent and Trademark Office, Office Action dated Feb. 28, 2011, pertaining to U.S. Appl. No. 12/048,764, 12 pages.
European Patent Office, Extended European Search Report—European Application No. 10181743.5-2310, dated Mar. 11, 2011, 6 pages.
Birnbaum et al., "Computer-Assisted Orthopedic Surgery With Individual Templates and Comparison to Conventional Operation Method", Spine, vol. 26, No. 4, pp. 365-369, Feb. 2001.
Brandt et al., In German: "CRIGOS—Development of a Compact Robot System for Image-Guided Orthopedic Surgery," Der Orthopäde, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," Der Orthopäde, Springer-Verlag, vol. 29, No. 7, pp. 645-649 (Jul. 2000).
CAOS, "MIS meets CAOS Spring 2005 Symposium Schedule", CAOS Spring 2005 Symposium, pp. 1-9, May 19, 2005.
Chelule et al., "Patient-Specific Template to Preserve Bone Stock in Total Knee Replacement: Preliminary Results", $15^{th}$ Annual ISTA Symposium, Sep. 2002, 1 page.
Chelule et al., "Computer Aided Design of Personalized Jigs in Total Knee Replacement", $3^{rd}$ Annual Meeting of CAOS Int'l Proc., Spain, Jun. 18, 21, 2003, pp. 58-59.
Froemel et al., "Computer Assisted Template Based Navigation for Total Knee Replacement", Documents presented at CAOS on Jun. 17, 2001, 4 pages.
Hafez et al., "Computer Assisted Total Knee Replacement: Could A Two-Piece Custom Template Replace The Complex Conventional Instrumentations?" Session 6: Novel Instruments; Computer Aided Surgery, Session 6, vol. 9, No. 3, pp. 93-94 (Jun. 2004).
Hafez et al., "Computer-assisted Total Knee Arthroplasty Using Patient-specific Templating," Clinical Orthopaedics and Related Research, No. 444, pp. 184-192 (Mar. 2006).
Hafez et al., "Computer Assisted Total Knee Replacement: Could a Two-Piece Custom Template Replace the Complex Conventional Instrumentations?", $4^{th}$ Annual Meeting of CAOS Int'l Proc., Chicago, Jun. 16-19, 2004, pp. 63-64.
Hafez et al., "Computer-Assisted Total Hip Arthroplasty: The Present and the Future", Future Rheumatol., vol. 1, pp. 121-131, 2006.
Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.

Portheine, In German: "Model-Based Operation Planning in Orthopedic Surgery", Thesis, RWTH Aachen University, Apr. 22, 2004, 90 pages.

Portheine, English Translation with Certification: "Model-Based Operation Planning in Orthopedic Surgery", Thesis, RWTH Aachen University, Apr. 22, 2004, 170 pages.

Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.

Radermacher et al., "Computer Assisted Matching of Planning and Execution in Orthopedic Surgery", IEEE, EMBS, San Diego, 1993, pp. 946-947.

Radermacher, "Computer Assisted Matching of Planning and Execution in Orthopedic Surgery", Slide Presentation, San Diego, Nov. 29, 1993, 22 pages.

Radermacher et al., "Computer Integrated Advanced Orthopedics (CIAO)", 2$^{nd}$ European Conference on Eng. And Med., presented Apr. 26, 1993, 12 pages.

Radermacher et al., "Surgical Therapy Technology", Helmholtz-Institut Aachen Research Report, 1993-1994, pp. 189-219.

Radermacher et al., "Computer Assisted Orthopedic Surgery By Means of Individual Templates •Aspects and Analysis of Potential Applications •" *Proceedings of the First International Symposium On Medical Robotics and Computer Assisted Surgery,* vol. 1: Sessions I-III, MRCAS '94, Pittsburgh, PA, pp. 42-48 (Sep. 22-24, 1994).

Radermacher, "Image Guided Orthopedic Surgery with Individual Templates", Helmhotz-Institute for Biomed. Eng., 2 pages, 1997.

Radermacher et al., In German: "Computer-assisted operative interventions in orthopedics—are there prospects for endoprosthetics as well?", Prac. Ortho., vol. 27, pp. 149-164, 1997.

Radermacher et al., English Translation with Certification: "Computer-assisted operative interventions in orthopedics—are there prospects for endoprosthetics as well?", Prac. Ortho., vol. 27, pp. 1-17, 1997.

Radermacher et al., "Computer Based Decision Support for the Planning of Contact Faces for Manual Registration with Individual Templates", Helmholtz-Institute for Biomed. Eng., 7 pages, 1997-1998.

Radermacher, In German: "Computer-Based Decision Support in the Selection and Evaluation of Contact Surfaces for Manual Referencing", Lecture presented at Helmholtz Meeting '98 and OSS '98, 7 pages.

Radermacher, English Translation with Certification: "Computer-Based Decision Support in the Selection and Evaluation of Contact Surfaces for Manual Referencing", Lecture presented at Helmholtz Meeting '98 and OSS '98, 8 pages.

Radermacher et al., In German: "Computer-Assisted Planning and Operation in Orthopedics", Orth. Prac. 36$^{th}$ year, pp. 731-737, Dec. 2000.

Radermacher et al., English Translation with Certification: "Computer-Assisted Planning and Operation in Orthopedics", Orth. Prac. 36$^{th}$ year, pp. 731-737, Dec. 2000.

Radermacher, "Template Based Navigation—An Efficient Technique for Hip and Knee Surgery", CAOS First Asian Meet, India, Mar. 27-28, 2004, pp. 44-50.

Rau et al., "Small and Neat", Medical Tech. Int'l, pp. 65, 67 and 69, 1993-1994.

Schiffers et al., In German: "Planning and execution of orthopedic surgery using individualized templates," *Der Orthopäde,* Springer-Verlag, vol. 29, No. 7, pp. 636-640, (Jul. 2000).

Schiffers et al., English Translation with Certification: "Planning and execution of orthopedic surgery using individualized templates," *Der Orthopäide,* Springer-Verlag, vol. 29, No. 7, pp. 636-640, (Jul. 2000).

Schkommadau et al., "Clinical Application of Individual Templates for Pedicle Screw Placement in Comparison to Computer Navigation", Poster presented at CAOS, Feb. 18, 2000, 1 page.

Schkommadau et al., In German: "Clinical Experience With the Individual Template Technique", Orth. Prac., vol. 37, No. 1, pp. 19-22, 2001.

Schkommadau et al., English Translation with Certification: "Clinical Experience With the Individual Template Technique", Orth. Prac., vol. 37, No. 1, pp. 19-22, 2001.

Seel et al., "Three-Dimensional Planning and Virtual Radiographs in Revision Total Hip Arthroplasty for Instability", Clinical Orthopaedics and Related Research, No. 442, pp. 35-38, Jan. 2006.

Staudte et al., In German: "Computer-Assisted Operation Planning and Technique in Orthopedics", North Rhine-Westphalia Acad. For Sciences, Lecture N.444, ISSN 0944-8799, 2000, 17 pages.

Staudte et al., English Translation with Certification: "Computer-Assisted Operation Planning and Technique in Orthopedics", North Rhine-Westphalia Acad. For Sciences, Lecture N.444, ISSN 0944-8799, 2000, 34 pages.

Thoma et al., In German: "Use of a New Subtraction Procedure Based on Three-Dimensional CT Scans for the Individual Treatment of Bone Defects in the Hip and Knee," *Journal DGPW,* No. 17, pp. 27-28 (May 1999).

Thoma et al., English Translation with Certification: "Use of a New Subtraction Procedure Based on Three-Dimensional CT Scans for the Individual Treatment of Bone Defects in the Hip and Knee," *Journal DGPW,* No. 17, pp. 27-28 (May 1999).

Thoma et al., In German: "Custom-made knee endoprosthetics using subtraction data of three-dimensional CT scans—A new approach," *Der Orthopäde,* Springer-Verlag, vol. 29, No. 7, pp. 641-644, (Jul. 2000).

Thoma et al., English Translation with Certification: "Custom-made knee endoprosthetics using subtraction data of three-dimensional CT scans—A new approach," *Der Orthopäde,* Springer-Verlag, vol. 29, No. 7, pp. 641-644, (Jul. 2000).

European Patent Office, European Search Report—Application No. 09716738.1 dated Feb. 6, 2012, 10 pages.

European Patent Office, Extended European Search Report—Application No. 10181149.5-1526 dated Apr. 19, 2012, 9 pages.

European Patent Office, Extended European Search Report—Application No. 10181198.2-1526 dated Apr. 19, 2012, 9 pages.

United States Patent and Trademark Office, Office Action dated Apr. 20, 2011, pertaining to U.S. Appl. No. 12/135,612, 13 pages.

United States Patent and Trademark Office, Office Action dated Sep. 26, 2011 pertaining to U.S. Appl. No. 12/048,764, 9 pages.

United States Patent and Trademark Office, Office Action dated Oct. 23, 2009, pertaining to U.S. Appl. No. 10/764,010, 13 pages.

United States Patent and Trademark Office, Office Action dated Jan. 9, 2009, pertaining to U.S. Appl. No. 10/764,010 11 pages.

Bromberg & Sunstein LLP, Response to Office Action dated Jan. 9, 2009, pertaining to U.S. Appl. No. 10/764,010, 25 pages.

United States Patent and Trademark Office, Office Action dated May 17, 2010, pertaining to U.S. Appl. No. 10/764,010, 12 pages.

Sunstein Kann Murphy & Timbers LLP, Response to Office Action dated May 17, 2010, pertaining to U.S. Appl. No. 10/764,010, 21 pages.

United States Patent and Trademark Office, Notice of Allowance dated Dec. 16, 2010, pertaining to U.S. Appl. No. 10/764,010, 11 pages.

United States Patent and Trademark Office, Notice of Allowance dated Aug. 5, 2011, pertaining to U.S. Appl. No. 10/764,010, 14 pages.

Sunstein Kann Murphy & Timbers LLP, Amendment dated Jun. 28, 2010 pertaining to U.S. Appl. No. 11/410,515, 16 pages.

United States Patent and Trademark Office Office, Action dated Oct. 6, 2010 pertaining to U.S. Appl. No. 11/410,515, 20 pages.

Sunstein Kann Murphy & Timbers LLP, Amendment dated Apr. 6, 2011 pertaining to U.S. Appl. No. 11/410,515, 12 pages.

Sunstein Kann Murphy & Timbers LLP, Preliminary Amendment dated Jul. 31, 2009, pertaining to U.S. Appl. No. 11/739,326, 19 pages.

United States Patent and Trademark Office, Office Action dated Apr. 20, 2010, pertaining to U.S. Appl. No. 11/739,326, 13 pages.

Sunstein Kann Murphy & Timbers LLP, Response to Office Action dated Apr. 20, 2010, pertaining to U.S. Appl. No. 11/739,326, 22 pages.

United States Patent and Trademark Office, Notice of Allowance dated Nov. 24, 2010, pertaining to U.S. Appl. No. 11/739,326, 8 pages.

Sunstein Kann Murphy & Timbers LLP, Preliminary Amendment dated Jul. 31, 2009 pertaining to U.S. Appl. No. 11/769,434, 44 pages.

United States Patent and Trademark Office, Office Action dated Aug. 2, 2010 pertaining to U.S. Appl. No. 11/769,434, 83 pages.

Sunstein Kann Murphy & Timbers LLP, Amendment dated Feb. 2, 2011 pertaining to U.S. Appl. No. 11/769,434, 44 pages.

Sunstein Kann Murphy & Timbers LLP, Preliminary Amendment dated Aug. 12, 2011, pertaining to U.S. Appl. No. 13/017,886, 13 pages.

United States Patent and Trademark Office, Office Action dated Jun. 23, 2011 pertaining to U.S. Appl. No. 11/410,515, 13 pages.

United States Patent and Trademark Office, Office Action dated Jan. 13, 2012 pertaining to U.S. Appl. No. 12/776,840, 10 pages.

United States Patent and Trademark Office, Office Action dated Jan. 26, 2012, pertaining to U.S. Appl. No. 12/139,324, 14 pages.

United States Patent and Trademark Office, Office Action dated May 31, 2012, pertaining to U.S. Appl. No. 12/398,753, 7 pages.

United States Patent and Trademark Office, Office Action dated Jun. 5, 2012, pertaining to U.S. Appl. No. 12/776,984, 7 pages.

\* cited by examiner

PATIENT-SPECIFIC JOINT ARTHROPLASTY DEVICES FOR LIGAMENT REPAIR

CROSS-REFERENCE TO RELATED APPLICATIONS

This application claims the benefit of and priority to U.S. Provisional Patent Application Ser. No. 61/169,823, entitled "Patient-Specific Joint Arthroplasty Devices for Ligament Repair," filed Apr. 16, 2009.

In addition, this application is a continuation-in-part of U.S. patent application Ser. No. 11/671,745, entitled "Patient Selectable Joint Arthroplasty Devices and Surgical Tools," filed Feb. 6, 2007 (the '745 application).

The '745 application claims the benefit of: U.S. Ser. No. 60/765,592, entitled "Surgical Tools for Performing Joint Arthroplasty," filed Feb. 6, 2006; U.S. Ser. No. 60/785,168, entitled "Surgical Tools for Performing Joint Arthroplasty," filed Mar. 23, 2006; and U.S. Ser. No. 60/788,339, entitled "Surgical Tools for Performing Joint Arthroplasty," filed Mar. 31, 2006.

Each of the above-described applications is hereby incorporated by reference in its entirety for all purposes, and this application claims priority to the applications listed above.

TECHNICAL FIELD

The embodiments described herein relate to orthopedic methods, systems and devices for surgical procedures related to joint ligaments. Some of the embodiments include surgical molds designed from patient-specific data to facilitate the repair or replacement of such ligaments.

BACKGROUND

There are a growing number of cases of surgical procedures performed to repair, reconstruct, replace, or otherwise treat ligaments, such as anterior cruciate ligaments ("ACL") and posterior cruciate ligaments ("PCL"). However, surgeons performing such procedures have difficulty, for example, in properly placing grafts or performing other surgical steps.

In the case of ACL and PCL grafts, placement of the associated tunnels to house the grafts can be difficult. For example, grafts placed too far anteriorly on the femur are reportedly a common cause of failure in ACL reconstruction. Some studies suggest that more precise placement of the femoral tunnel would improve kinematics. More accurate placement of the tibial and femoral tunnels may reduce the incidence of graft failure and may reduce long-term degeneration observed after reconstruction. There are other difficulties associated with such procedures. For example, in some cases it can be difficult to locate the tissue from which a graft is to be extracted, or to properly size the graft.

SUMMARY

The embodiments described herein provide novel devices and methods for performing surgical procedures to replace, repair or otherwise treat ligaments associated with bone joints.

In one aspect, certain embodiments relate to a method for ligament repair includes obtaining electronic image data of at least one surface associated with a ligament. A first template is created based, at least in part, on the image data. The first template has at least one contact surface that conforms to at least a portion of the surface. The first template includes at least one guide for directing movement of a surgical instrument involved with the ligament repair.

In some embodiments, the ligament may be an anterior cruciate ligament or a posterior cruciate ligament. The method may further include determining a tunnel site for a ligament graft. Determining the tunnel site may include identifying an origin of the ligament on a first articular surface and an insertion position onto a second articular surface opposing the first articular surface. Determining the tunnel site may include identifying at least one of a bony landmark and a remainder of a ligament based on the image data. The surface may be adjacent to the tunnel site, or a non-weight bearing surface. The first template may include one or more pin and/or drill guide apertures, the method further including positioning the template such that the at least one contact surface contacts the at least a portion of the surface, and creating (e.g., drilling) a ligament tunnel, for example, wherein the drilling is guided by the drill guide aperture. At least one of the shape, position and orientation of a pin and/or drill guide aperture on the first template may be based, at least in part, on a distance of the tunnel to adjacent cortical bone. The drill guide aperture may include a stop, such that a desired drill depth is obtained. The image data may be obtained preoperatively. The image data may be obtained by a CT scan or an MRI scan. The image data may be obtained in joint flexion, joint extension, joint abduction, joint adduction, and/or joint rotation. The method may further include identifying a graft harvest site based on the image data, and using the first template to guide harvesting of at least one of ligament and bone from the graft harvest site. The method may further include cross-referencing a second template to the first template to align position of the second template on a second surface associated with the ligament, the second template including at least one guide, and directing movement of the instrument using the at least one guide of the second template relative to said guide. The first and second surfaces may be opposing articular surfaces. The first surface may be a femoral surface and the second surface may be a tibial surface. The first template may include a tissue retractor. The tissue retractor may be a flange or an extender on the template. The template may be used for single bundle or a double bundle ligament reconstruction.

In some embodiments the method may further include obtaining electronic image data of the joint and determining a shape of the at least one contact surface of the first template based, at least in part, on electronic image data. Stabilizing may include using k-wires, a screw, an anchor, and/or a pin or drill bit left in place on the joint. Stabilizing may include positioning the contact surface on at least one or more concavities and convexities on the joint. Stabilizing may include positioning the contact surface on at least one concavity and at least convexity on the joint. Stabilizing may include positioning the contact surface, at least partially, on an arthritic portion of the joint. Stabilizing may include positioning the contact surface, at least partially, on an interface between a normal and an arthritic portion of the joint. Stabilizing may include positioning the contact surface, at least partially, against an anatomic feature. The anatomic feature may be a trochlea, an intercondylar notch, a medial condyle and a lateral condyle, a medial trochlea and a lateral trochlea, a medial tibial plateau and a lateral tibial plateau, a fovea capities, an acetabular fossa, a tri-radiate cartilage, an acetabular wall, or an acetabular rim. Positioning the contact surface on the surface of the joint may include positioning the contact surface on, at least partially, a normal portion of the joint. Determining the position of the guide on the template may be based, at least in part, on ligament balancing and/or to optimize at least one of flexion and extension gap. The method may further include adjusting the position of the guide relative to the joint intraoperatively using, for example, a spacer, a ratchet device, and a pin that allows rotation.

In some embodiments, determining the desired femoral component rotation may include measuring one or more anatomic axes and/or planes relevant to femoral component rotation. The one or more anatomic axes and/or planes may include a transepicondylar axis, the Whiteside line, and/or the posterior condylar axis. The guide may direct a femoral cut, the method further comprising rotating the template so that the femoral cut is parallel to a tibial cut with substantially equal tension medially and laterally applied from medial and lateral ligaments and soft tissue.

In some embodiments, determining the desired tibial component rotation may include measuring one or more anatomic axes and/or planes relevant to tibial component rotation. The one or more anatomic axes and/or planes may include an anteroposterior axis of the tibia and/or the medial one-third of the tibial tuberosity. The guide may direct a femoral cut, the method further comprising rotating the template so that the femoral cut is parallel to a tibial cut with substantially equal tension medially and laterally applied from medial and lateral ligaments and soft tissue.

In some embodiments, a method for joint arthroplasty includes providing a template that includes at least one surface for engaging a surface of a joint based, at least in part, on substantially isotropic input data. The surface can substantially match (i.e., conform to or register) one or more portions of the joint surface or of the entire joint surface. The template can include at least one guide for directing movement of a surgical instrument.

In some embodiments, the input data can be acquired using fusion of image planes, or substantially isotropic MRI and spiral CT.

In any of the embodiments and aspects described herein, the joint can be, without limitation, a knee, shoulder, hip, vertebrae, elbow, ankle, foot, toe, hand, wrist or finger.

Some embodiments can include various additional features such as an intraoperative adjustment of various dimensions, orientations or relative locations. For example, the instruments can position one or more tunnels, while tunnel orientation can be determined intraoperatively based on graft length and location. The instruments can also position an entry for a tunnel and determine tunnel orientation, with optional intraoperative adjustment.

In some embodiments, a first tunnel can be used to connect to and or provide a reference for a second tunnel associated with the same articular surface or associated with a different articular surface.

In some embodiments, the kinematics of the joint can be evaluated and/or improved, for example, during the procedure or prior to the procedure, e.g., by evaluating images and/or models of the joint. For example, a simulation can be performed showing a patient's bio-motion and the kinematics can be superimposed onto imaging data to assess the best possible graft tunnel placement that provides, for example, expected graft length, expected graft thickness, expected graft strength, and/or one or more other features.

In some embodiments, a finite element analysis can be performed based on the imaging data, kinematic information and/or models of a patient's joint, including, without limitation, models of joint motion and/or joint structure. For example, the finite element analysis can be performed to determine bone strength, in particular for a double bundle technique to ensure sufficient bone material between tunnels. The finite element analysis can include an analysis of one or more parameters, including, without limitation, one or more of graft length, graft thickness, bone tunnel length, bone tunnel thickness, patient weight, height, gender, forces with various activities, bone volume, bone thickness, bone structural parameters, and bone density. A multivariate analysis can be performed for various loading conditions to identify the best possible tunnel location with the lowest probability of future failure.

Some embodiments can include sensors, optical markers, RF markers and other additional devises and components to aid in, for example, balancing, surgical navigation, and/or one or more other processes and objectives.

Some embodiments are described in greater detail below. It is to be understood that the features of the various embodiments described herein are not mutually exclusive and may exist in various combinations and permutations.

BRIEF DESCRIPTION OF THE DRAWINGS

The foregoing features can be more readily understood by reference to the following detailed description, taken with reference to the accompanying drawings, in which.

DETAILED DESCRIPTION

Figure 1:
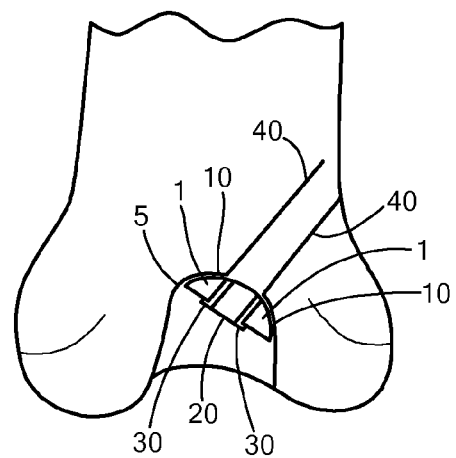
FIGS. 1-3 illustrate the use of guidance templates for performing ligament repair, in accordance with some embodiments of the invention.

Surgical tools and other devices may be designed from an individual patient's anatomy to provide devices that have a custom fit or perform a customized function for that patient, that provide improved or optimized anatomical structure for that patient, that provide improved or optimized kinematics for that patient, and/or that are provided for use with standard implants, tools, devices, surgical procedures, and/or other methods. These surgical tools, including, without limitation, alignment guides, are particularly suited for the repair, replacement, or other treatment of ligaments, including, without limitation, an anterior cruciate ligament ("ACL") and/or posterior cruciate ligament ("PCL").

These surgical tools, for example, alignment guides and other devices may include, without limitation, templates, jigs and/or molds, including guidance molds. In the specification, the terms "template," "jig," "mold," "guidance mold," and "guidance template," may be used interchangeably within the detailed description and appended claims to describe specific embodiments of the larger class of surgical tools unless the context indicates otherwise.

Patient-specific surgical tools and other devices include a range of embodiments. For example, such tools and devices may be completely or partially customized to a patient, as in the case of an alignment guide that is form-fitted to a surface of a joint and the location of a ligament. Additionally, other tools and devices may include only one or a few dimensions or characteristics designed from the patient-specific data, as in the case of an implant that has a surface with radius of curvature in the coronal plane, but not the sagittal plane, that is based on a corresponding radius of curvature of a surface of the patient's anatomy in the coronal plane. In some embodiments, the tools and devices may be designed, at least in part, based on the patient's specific data to incorporate one or more design characteristics that produce an ideal, optimized or improved anatomical structure, kinematic function, and/or other surgical result. These cases are exemplary only, and many other embodiments and combinations of embodiments are possible.

Among other things, the techniques, tools, implants, devices and methods described herein allow for the customization of cartilage and ligament repair to suit a particular subject, for example in terms of size, cartilage thickness and/or curvature. Thus, the embodiments described herein provide, among other things, for minimally invasive methods for ligament repair, replacement and treatment. Preferred embodiments are minimally invasive, although the concepts disclosed herein can be used in conjunction with more invasive techniques. Additionally, unlike with current techniques, preferred embodiments described herein can help produce efficient and precise surgical steps by providing surgical tools that achieve an exact or near anatomic match between the implant and the surrounding or adjacent cartilage and/or subchondral bone as well as precise location of and alignment with anatomical landmarks associated with ligaments to produce a reliable and improved surgical result.

1. Ligament Repair, Replacement and/or Treatment

Guidance molds can be utilized in planning the approach and preparing surgical intervention, and in conducting the surgical intervention, for ligament repair and replacement. In some embodiments, the ACL or PCL can be repaired, replaced, reconstructed or otherwise treated using one or more guidance molds in one or more steps of the procedure. Other tendon and ligament injuries, for example, including the rotator cuff, the ankle tendons and ligaments that are highly prevalent and frequent, also can be addressed using the embodiments described herein.

1.1 ACL Treatment

The ACL is a continuum of fibers having no distinct bundle morphologic features. The microanatomy comprises of multiple collagen fibers, grouped into larger fascicles. Despite the lack of anatomic delineation, the fiber arrangement has been "functionally" divided into two subdivisions or bundles: an anteromedial band and a posterolateral band. The fibers of the anteromedial band pass from the proximal part of the femoral attachment to the anteromedial aspect of the tibial footprint. The posterolateral band fibers attach distally to the femur and posterolaterally to the tibia. The posterolateral band is taut when the knee is extended, and the anteromedial band becomes taut when the knee is flexed. Because of its internal architecture and attachment sites on the femur and tibia, the ACL provides restraint to anterior translation and internal rotation of the tibia, varus and valgus angulation, and hyperextension of the knee.

Current estimates indicate that 100,000 ACL reconstruction operations are performed annually in the United States. Many of these injuries occur during sporting activities that involve deceleration, twisting, cutting, and jumping movements. The ligament fails as a consequence of excessive valgus stress, forced external rotation of the femur on a fixed tibia with the knee in full extension, or forced hyperextension. The spectrum of ACL injury ranges from a partial sprain (grade I or II) to complete disruption (grade III).

Because of its intraarticular location, the ACL has poor healing potential. Extraarticular ligaments heal by progressing through a series of inflammatory, proliferative, and remodeling phases, which result in the formation of organized scar tissue. This process is incited by the formation of a localized hematoma. In contrast, when the ACL is torn, its synovial envelope is damaged, and blood dissipates within the joint. Without the formation of a blood clot, the normal sequence of soft tissue repair cannot initiate. The ruptured ACL does not form a bridging scar after complete disruption. Instead, a layer of synovial tissue forms over the damaged surface and the ruptured ends retract.

Without treatment, a complete ACL injury can result in progressively increasing symptomatic knee instability, which inflicts recurrent intraarticular damage and eventually causes osteoarthritis.

Typical treatment of an ACL injury can include one or more of the following steps:

1. Knee evaluation and confirmation of ACL rupture;
2. Graft harvesting;
3. Arthroscopic documentation and treatment of intraarticular disease;
4. Preparation of the intercondylar notch;
5. Osseous tunnel placement;
6. Graft implantation and fixation; and
7. Wound closure and postoperative issues.

Descriptions of typical features of each of these steps are included in the following subsections.

1.1.1 Knee Evaluation

Knee evaluation can include preoperatively evaluating and comparing the injured knee and the contralateral knee with the patient under anesthesia, for example, by means of physical examination and a KT-1000 knee arthrometer. When complete rupture of the ACL is clinically obvious, an autograft can be harvested in advance of the arthroscopic portion of the surgical procedure.

1.1.2 Graft Harvesting

Graft selection can depend on the individual surgeon's and patient's preferences. Frequently, an autograft is harvested from the middle third of the patient's patellar tendon with bone plugs at both ends, although other sources of autograft, allograft, or xenograft may be used. When harvesting the middle third of the patient's patellar tendon, a graft width of 40% or less of the overall patellar tendon width can be targeted and the scalpel blades are set accordingly. For example, when the tendon width is at least 25 mm, the blades are set 10 mm apart. In smaller patients, slightly less graft width can be targeted. Beginning at a bony attachment, the central third of the tendon can be incised in the line of its fibers. Electrocautery then can be used to delineate the bone-tendon junctions and to outline the margins of the bone plugs. It is advantageous for a technique used to harvest the bone plugs to reproducibly obtain a plug that fits snugly into the osseous tunnels with minimal contouring to allow secure fixation. In addition, it is advantageous to implement a bone plug harvesting technique that minimizes the risk of patella fracture at the site of harvest. A circular oscillating saw (Stryker), which provides cylindrical bone plugs of varying diameter (9, 10, or 11 mm), can be used, for example, with a saw blade 10 mm in diameter. This device affords the following advantages: (a) ease and rapidity of harvest, (b) reproducible cylindrical bone plug 1 mm smaller in diameter than the corresponding osseous tunnel, (c) decreased stress riser at the patella harvest site, and (d) ease of graft insertion because of uniform sizing. However, since this device and others like it are manually placed onto the patient's bone, the device placement and bone plug placement can vary from the surgeon's intended placement or an ideal placement Once harvested, the autograft can be prepared and shaped for implantation at a side table by the surgeon or by an assistant while the surgeon prepares the osseous tunnels to receive the autograft.

Preferably, the bone plug harvested from the tibia measures about 25 mm in length and the bone plug harvested from the patella measures about 20 to 22 mm. A simulation of bone plug passage through the osseous tunnels can be performed using cylindrical sizers. The bone plugs can be trimmed as needed or desired until they slide easily through the appropriate sizer. The smaller bone plug, typically from the patella, is placed in the femoral tunnel. A single hole, for example, using a 3/32 drill bit hole, is established through the cortical surface of the bone plug, through which a suture is threaded. The hole is sited fairly close to the tip of the bone plug, to provide better directional control during graft passage into the femoral tunnel. Three evenly spaced holes are made in the tibial bone plug and are threaded with sutures. The holes are oriented perpendicular to each other to minimize the chance of suture laceration during interference screw insertion. The total length of the typical bone-patellar tendon bone graft is usually about 90 to 105 mm after preparation. The desired length of the tibial tunnel can be calculated by subtracting the length of the femoral tunnel and intraarticular length from the overall graft length. One means to address length mismatch between the graft and tunnel involves harvesting additional bone plug material from the tibia for inserting into the femoral tunnel, thus effectively recessing the entire graft further into the femur and reducing the potential for the graft to protrude from the tibia. This technique can effectively recess the graft up to 8 mm into the femoral tunnel with insertion of a tibial bone block into the tunnel behind the bone plug.

1.1.3 Documentation and Treatment of Intraarticular Disease

The intraarticular portion of the surgical procedure can be performed while the graft is prepared at a side table by an assistant. Typically, an arthroscope is inserted into an anterolateral portal created by retracting the skin flap to expose the lateral border of the patella tendon. An anteromedial portal can be made in a similar way, and both portals can be placed within the margins of the existing skin incision. Separate standard arthroscopic portals can be included when using alternative grafts. ACL reconstruction typically includes high fluid flows, which can be achieved through a separate cannula or by a pump through the arthroscope. A thorough diagnostic arthroscopic examination can be performed to confirm the torn ACL and to assess the status of the menisci and articular cartilage. Each intraarticular structure can be probed, for example, using a hook, and sequential photographic images can be taken for documentation purposes. Preferably, any associated intraarticular injuries are treated before proceeding with ligament reconstruction. For example, meniscal tears can be repaired or resected and articular cartilage damage can be documented and treated if deemed appropriate, for example, by chondroplasty or microfracture.

1.1.4 Preparation of the Intercondylar Notch

In some embodiments, remnants of the torn ACL can be debrided using a full-radius resector such that the tibial footprint can be clearly identified. The ligamentum mucosum can be removed to enhance visualization. The infrapatellar fat pad is seldom resected, and the posterior cruciate ligament (PCL) is typically protected. Notchplasty can begin with debridement of soft tissue and periosteum from the lateral wall of the notch, for example, using an oscillating resector for soft tissue removal under direct visualization. The entire surface of the lateral wall that involves the opening to the osseous tunnel can be debrided. Once the notch has been adequately debrided of soft tissue, an assessment can be made regarding the need for additional bony notchplasty, which may be performed if there is difficulty in visualizing the lateral wall or if the presence of notch osteophytes may impinge and guillotine the ACL graft. The procedure can be carried out using an arthroscopic bur or a full-radius resector. If t notch widening is desired, a Y4-inch curved osteotome may be introduced through a portal, and the large bone fragments may be removed with a grasper. Minimal articular cartilage removal is desirable. When relying on visual landmarks for placement of pins, drills and other tools, for example, for placing a pin or drill to create the osseous tunnel, additional material may need to be removed for proper identification of the landmarks. For example, it is advantageous for the posterior margin of the notch to be clearly identified to avoid misinterpreting the so-called "resident's ridge" as the over the-top position. This error in visual landmark selection may cause the femoral tunnel to be placed more anteriorly than desired in a procedure that relies solely on visual identification of landmarks.

1.1.5 Osseous Tunnel Placement and Preparation

The selection of ideal osseous tunnel sites is a significant step in ACL reconstruction. The normal ACL is composed of a large number of fibers. Each fiber is a different length, has a different origin and insertion, and is under different tension during the range of motion of the knee. The graft replacing the ACL includes parallel fibers. Even with optimal selection of the placement of the osseous tunnels, the fibers of the graft can undergo length and tension changes with range of motion. Therefore, the ACL replacement may not duplicate the original ligament. However, placing the center of the osseous tunnels at the most isometric points maximizes the stability that can be obtained during motion.

The site for the femoral tunnel is selected once the notch has been prepared. In traditional methods, the placement of the tunnel requires visualization of the over-the-top position, which can be improved by flexing the patient's knee to 70 degrees or more.

If interference screw fixation is desired, a site selection can result in an osseous tunnel with at least a 1- to 2 mm thick posterior cortical wall to provide a posterior buttress for the interference screw and thereby help to prevent posterior wall blowout.

In order to locate the desired center of the femoral tunnel, one or more placement guides can be used, for example, that key off the over-the-top position. For example, as described more fully below, one or more templates having a surface that conforms to a surface of the patient's anatomy and a guide for establishing the osseous tunnel in the desired location can be used. The conforming surface of the template can be created, for example, based on image data of the patient's anatomy.

Using a template that conforms to the patient's anatomy, one or more of the osseous tunnel location, tunnel diameter and/or tunnel length can be predetermined precisely, for example, based on images of the patient's anatomy, and the features of the guide can be designed so that the desired location, diameter, and/or length are achieved. The guide can be inserted through an accessory anteromedial portal placed more inferiorly, just above the joint line and aligned so that the conforming surface on the guide engages the corresponding surface of the patient's anatomy. Optionally, the position of the guide can be verified visually and checked with a tool, for example, with a nerve hook, to confirm the correct position. Selecting the properly positioned femoral tunnel site ensures maximum postoperative knee stability.

The intraarticular site of the tibial tunnel can have less effect on changes in graft length, but its position can be important in preventing intercondylar notch impingement. The extraarticular opening of the tibial tunnel can be generally located at the center of the intraarticular opening immediately posterior to the anatomic center of the ACL tibial footprint. Four anatomic landmarks can be useful to locate the tibial tunnel center; the anterior horn of the lateral meniscus, the medial tibial spine, the PCL, and the ACL stump. The site can be located in the anteroposterior plane by extending a line in continuation with the inner edge of the anterior horn of the lateral meniscus. This point can be located 6 to 7 mm anterior to the anterior border of the PCL. In many procedures, this tunnel placement may allow the ACL graft, once in place, to touch the lateral aspect of the PCL but not be significantly deflected by it. Similarly, it should neither abrade nor impinge against the medial aspect of the lateral femoral condyle or the roof of the intercondylar notch when the knee is in full extension. Anterior graft placement can result in impingement and subsequent graft failure.

1.1.6 Graft Passage and Fixation

Under arthroscopic visualization, the graft is passed into the femoral tunnel with cephalad traction on the proximal suture. The cancellous surface is placed anterolaterally so the collagen fibers of the new ligament are posterior in the femoral tunnel. The graft is fully seated when the junction of the bone plug and ligament, marked earlier with a pen, is visualized at the tunnel mouth. Cannulated interference screws may be used for fixation of the graft, although other alternative fixation methods are available 1.1.7 Wound Closure and Post-Operative Issues In the final step of surgery, the bony defect created from the autologous graft, for example, in the patella, is grafted using the core of bone obtained from the tibial tunnel. Retinacular tissue can be closed over the defect to hold the graft in place. The patella tendon is loosely reapproximated to minimize any palpable gaps, without shortening the tendon. The para tendon, subcutaneous tissue, and skin are closed in separate layers. Following surgery, rehabilitation proceeds for several weeks. Post-operative complications relating to ACL reconstruction can include, for example, one or more of loss of motion, recurrent instability, as well as patellofemoral dysfunction, and pain.

Failure to regain full range of motion after ACL reconstruction can be related to surgical error in graft placement, arthrofibrosis, prolonged immobilization, or inadequate participation in a rehabilitation program. Technical errors that affect the range of knee motion include anterior placement of the tibial tunnel, graft impingement, and improper tensioning of the graft. Accordingly, accurate placement of the femoral tunnel can be important. If the femoral tunnel is sited too anteriorly, it may limit knee flexion, whereas if it is placed too far posteriorly, it can restrict knee extension. When the tibial tunnel is positioned too far anteriorly, the ACL graft may impinge against the intercondylar notch, thereby restricting knee extension. Over time, the notch has a guillotine effect on the graft and causes it to fail. An adequate notchplasty and careful selection of osseous tunnel sites can minimize the risk of impingement.

1.2 Patient-Specific Tools and Methods for ACL Procedures

In some embodiments described herein, guidance templates can be selected and/or designed to enable highly accurate, reproducible and minimally invasive graft tunnels in the femur and the tibia.

In one embodiment, imaging such as CT or MRI is performed pre-operatively. The images can be utilized to identify the origin of the ligament and its insertion onto the opposing articular surface, which in the case of an ACL is the tibia. Once the estimated location of the origin and the footprint, i.e., the insertion of the ligament, has been identified, guidance templates can be made to be applied to these areas or their vicinity. The ligament origin or insertion can be identified via their unique contour on the bone surface or by identifying ligament fiber remnants in the respective locations.

The guidance templates may be made to be sized and/or shaped to conform to (i.e., substantially match) the patient's articular surface, for example, adjacent to the intended tunnel location. For example, they may be made to be sized and/or shaped to conform to one or more the patient's bone and/or cartilage, for example, one or more of the patient's bone and/or cartilage surfaces outside the weight bearing zone, for example, in the intercondylar notch. In some embodiments, a template shape may be made to conform to one or more prominent or unique surface features or projections, for example, as identified in images of the patient's anatomy, osteophytes or other features. A guidance template for femoral or tibial tunnel placement for ACL repair may include blocks, attachments or linkages for reference points or guide aperture to guide and direct the direction and orientation of a pin and/or drill, and optionally, also a drill depth. Optionally, the guidance templates may be hollow or include openings. The guidance templates may be circular, semi-circular or ellipsoid. The guidance templates may have one or more openings to accommodate and/or guide a pin or drill.

In one embodiment, the guidance template is placed on, over or near the intended femoral or tibial entry point and subsequently a guide hole. Once proper anatomic or functional positioning has been achieved, the ligament tunnel can be created. The guidance template, its shape, position, and/or orientation, may be optimized to reflect the desired (e.g., preoperatively determined) tunnel location in the femur and the tibia, wherein the tunnel location, position, orientation and/or angulation is selected to achieve the best possible functional results. Additional considerations in placing the femoral or tibial tunnel can include a sufficient distance to the cortical bone in order to avoid failure or fracture of the tunnel. Placement can be optimized based on the anatomy visualized on the imaging test as well as biomechanical considerations, including finite element modeling that can optionally account for the material properties of bone and ligament replacement material.

Thus, optionally, the distance of the tunnel to the adjacent cortical bone and also other articular structures may be factored into the position, shape and/or orientation of the femoral or tibial guidance templates in order to achieve the optimal compromise between optimal ligament function and possible post-operative complications such as failure of the tunnel.

In one embodiment, the imaging test may be utilized to determine the origin and insertion of the ligament. This determination can be performed on the basis of bony landmarks identified on the scan, e.g., a CT scan or MRI scan. Alternatively, this determination can be performed by identifying ligament remnants, for example, in the area of the ligament origin and ligament attachment. By determining the origin and the insertion of the ligament the intended graft length may be estimated and measured. This measurement may be performed for different pose angles of the joint such as different degrees of flexion, extension, abduction, adduction, internal and external rotation.

In one embodiment, the imaging test may be utilized to identify the ideal graft harvest site wherein the graft harvest site can optionally be chosen to include sufficiently long ligament portion and underlying bone block proximally and distally in order to fulfill the requirement for graft length as estimated earlier based the imaging test and, optionally, functional simulations of kinematic performance, e.g., in flexion or extension. An additional guidance template, optionally with linkages, may be utilized to harvest the ligament and bone from the donor site in the case of an autograft. Optionally, guidance templates may also be utilized or designed or shaped or selected to guide the extent of an optional notchplasty. This can include, for example, the removal of osteophytes.

In the case of an ACL replacement, the guidance templates may in this manner optimize selection of femoral and tibial tunnel sites. Tunnel sites may even be optimized for different knee pose angles, e.g., joint positions, and different range of motion and kinematics including kinematic simulations. Selecting the properly positioned femoral tunnel site ensures maximum post operative knee stability.

The intra-articular site of the tibial tunnel has less effect on changes in graft length but its position can be optimized using proper placement, position, and shape of guidance templates to prevent intercondylar notch impingement.
Moreover, the guidance templates may include an optional stop for a drill, for example, to avoid damage to adjacent neurovascular bundles or adjacent articular structures, including the articular cartilage or other ligaments. Optionally, the guidance templates may also include a stop, for example, for a drill in order to include the drill depth.

The direction and orientation of the tibial tunnel and also the femoral tunnel may be determined with use of the guidance template, whereby it also can include selection of an optimal tunnel orientation in order to match graft length as measured pre-operatively with the tunnel length and the intra-articular length of the graft ligament.

In one embodiment, a tibial guidance template can be, for example, selected so that its opening is located at or immediately posterior to the anatomic center of the ACL tibial footprint. Anatomic landmarks may be factored into the design, shape, orientation, and position of the tibial guidance template, optionally. These include, without limitation, the anterior horn of the lateral meniscus, the medial tibial spine, the posterior cruciate ligament, and the anterior cruciate ligament stump.

The tunnel site may be located utilizing the guidance template in the anterior posterior plane by extending a line in continuation with the inner edge of the anterior horn of the lateral meniscus. This plane can be located six (6) to seven (7) millimeters anterior to the interior border of the PCL. The position, shape and orientation of the guidance template can be made to be sized and/or shaped so that the resultant tibial tunnel and the resultant location and orientation of the ACL graft, once in place, touch the lateral aspect of the PCL, but do not significantly deflect it. Similarly, the location of the tibial guidance template and the resultant ligament tunnel and the resultant location of the ACL graft, once in place, may be designed so that the graft neither abrades nor impinges against the medial aspect of the lateral femoral condyle or the roof of the intercondylar notch when the knee is at a particular angle, for example, in full extension. In this manner, highly accurate graft placement using patient-specific templates helps to avoid the problems of impingement and subsequent graft failure.

In one embodiment, pre-operative scans of the patient's anatomy can be evaluated to determine various values such as a maximal possible graft length, for example, of a patella tendon graft. If there is concern that the maximal graft length is not sufficient for the intended ACL replacement, the tunnel location and orientation, specifically the exits from the femur or the tibia can be altered and optimized in order to match the graft length with the tunnel length and intra-articular length.

In a preferred embodiment, the graft length is measured and/or simulated pre-operatively, for example, by measuring the optimal graft length for different flexion and extension angles or other kinematic simulations that merge the patient specific imaging data with kinematic data and simulations. Using this approach, an optimal position, shape, orientation and design of the guidance template may be derived at an optimal compromise between isometric graft placement, avoidance of impingement onto the PCL, and/or avoidance of impingement onto the femoral condyle, while optionally also maximizing achievable graft lengths.

Intraoperatively, the femoral and/or tibial guidance templates may include one or more intraoperatively adjustable features. These adjustable features, for example, that can allow movement of the template by one or two or more millimeters intervals in posterior or medial or lateral orientation, with resultant movement of the femoral or tibial tunnel. Additionally, intraoperative adjustment may also allow for rotation of the template, with resultant rotation of the resultant femoral or tibial tunnels.

A single template may be utilized to derive the femoral tunnel. A single template may also be utilized to derive the tibial tunnel. More than one template may be used on either side.

Optionally, the templates may include linkages, for example, for attaching additional measurement devices, guide wires, or other surgical instruments. Alignment guides including mechanical, electrical or optical devices may be attached or incorporated in this manner. Linkages can also be used to connect multiple templates on one articular side. Linkages can also be used to connect and or reference one or more templates on a first articular side with one or more templates on a second articular side. Linkages can be used for achieving smaller individual template component sizes. This can be advantageous for introducing the templates through a small portal or mini-incision or a bone tunnel. Optionally, the templates can then be connected or assembled inside the joint thereby enabling a minimally invasive including arthroscopic technique.

In one embodiment, a second articular surface, for example, an opposing articular surface, may be cross referenced against a first articular surface. For example, in the case of an ACL repair, the femoral tunnel may be prepared first using a guidance template, whereby the guidance template helps determine the optimal femoral tunnel position, location, orientation, diameter, and shape. The femoral guidance template may include a link inferiorly to the tibia or an attachable linkage, wherein said link or said attachable linkage may be utilized to determine the ideal articular entry point for the tibial tunnel. In this manner, the tibial tunnel can be created in at least one of an anatomic environment and a mechanical cross reference with the femoral tunnel. The reverse approach is possible, whereby the tibial tunnel is created first using the guidance template with a link or linkage to a subsequently created femoral tunnel. Creating the femoral or tibial tunnel in reference to each other advantageously helps reduce the difficulty in performing the ligament repair and also can improve the accuracy of the surgery in select clinical situations. In this manner, the templates can be used for initial first referencing of one or more bone tunnels, with subsequent optimization of tunnels on two opposing articular surfaces.

In one embodiment, the template for ligament repair may include optional flanges or extenders. For example, in some embodiments the flanges or extenders may have the function of tissue retractors. By having tissue retractor function, the intra-articular template for ligament repair can provide the surgeon with a clearer entry to the intended site of surgical intervention and improve visualization. Moreover, flanges or extenders originating from or attached to the guidance templates may also serve as tissue protectors, for example, protecting the posterior cruciate ligament, the articular cartilage, or other articular structures as well as extra-articular structures.

In one embodiment, an additional guidance template or linkages to a first or second articular guidance template can be utilized to place ligament attachment means, for example, interference crews.

If an allograft, xenograft, or artificial ligament replacement is chosen and the length and optionally, dimensions of it are known pre-operatively, additional adjustments may be made to the position, shape and orientation of the guidance templates and additional tunnels in order to match graft dimensions with tunnel dimensions and graft length with intrafemoral tunnel length, intra-articular length and/or intra-tibial tunnel length. Optionally, this adjustment and optimization can be performed for different pose angles of the joint, e.g., different degrees of flexion or extension.

Figure 2:
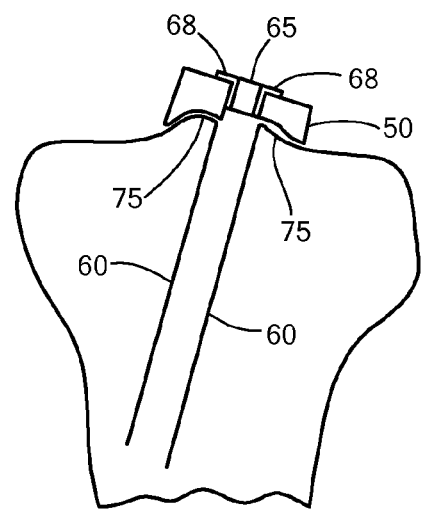
Figure 3:
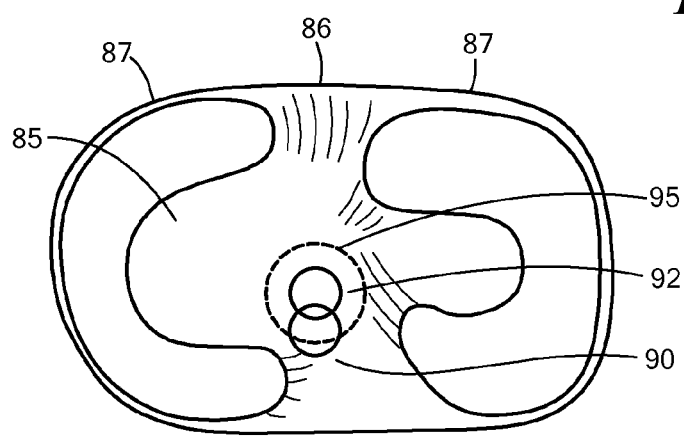
Figure 4:
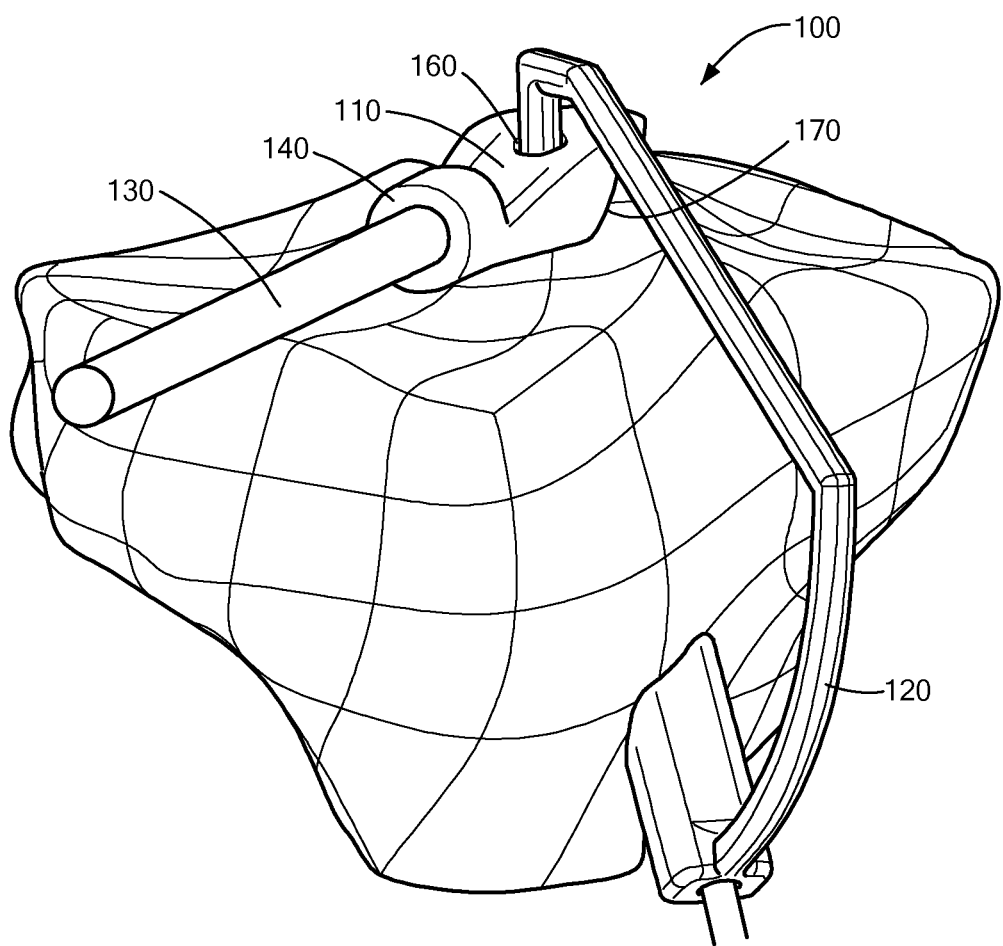
FIG. 4 is a side perspective view of an embodiment of a patient-specific instrument for use in creating (e.g., drilling) a tibial tunnel during an ACL procedure, in accordance with some embodiments of the invention.
Figure 5:
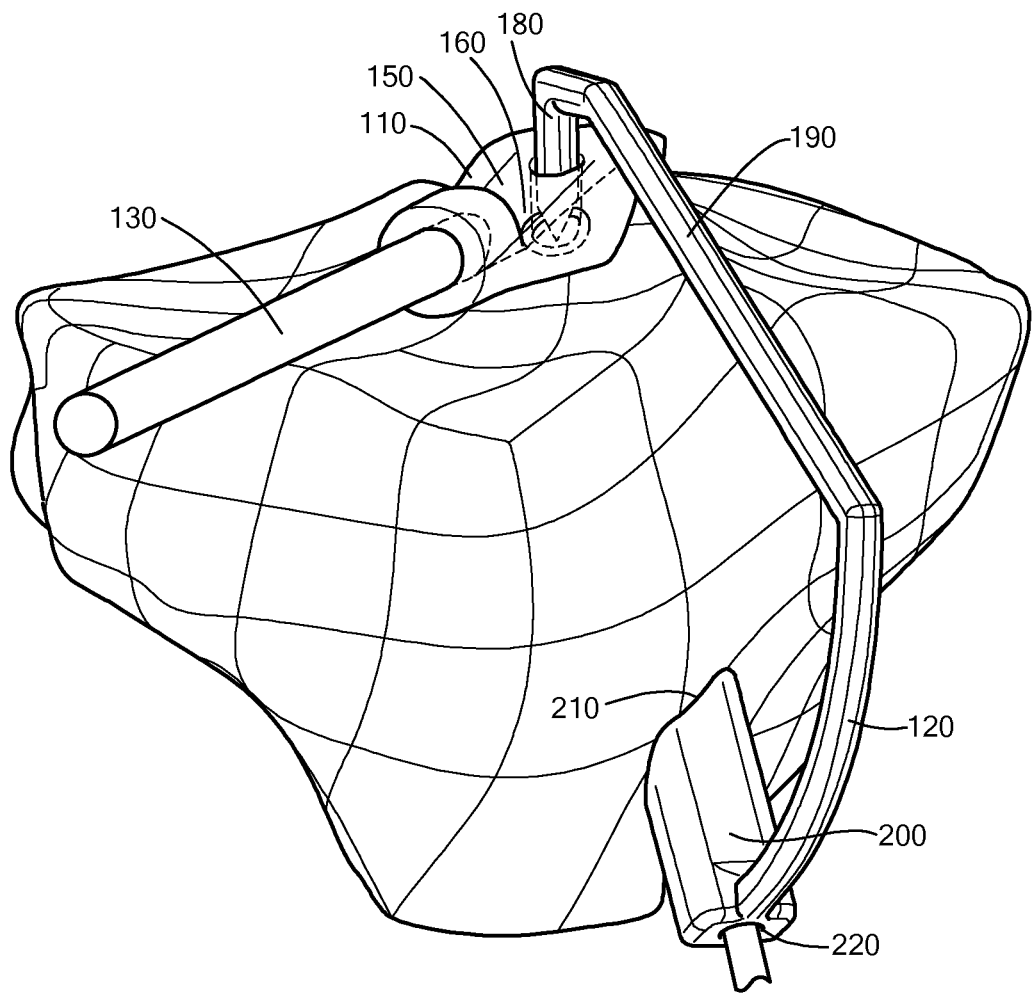
FIGS. 5-7 are side perspective views of the embodiment shown in FIG. 4, with a fitting component shown in a partially transparent view, in accordance with some embodiments of the invention.

FIGS. 1-3 illustrate an exemplary use of guidance templates for performing ligament repair; in this case repair of the anterior cruciate ligament (ACL). FIG. 1 shows a cross-sectional view of a femur and femoral guidance template. In particular, a guidance template 1 is placed in the intercondylar notch region 5. At least one surface 10 of the template 1 is sized and shaped to conform to (i.e., substantially matches) at least one or more portions of the notch 5 or the femur. The conforming shape is derived from the patient's imaging study such as a CT scan or MRI scan. The template 1 may be optionally placed against the trochlea and/or the femoral condyle (not shown). The mold 1 includes an opening 20 and, optionally, metal sleeves 30, wherein the position, location and orientation of the opening 20 and/or the metal sleeves 30 determine the position and orientation of the femoral graft tunnel 40.

FIG. 2 shows a cross-sectional view of a tibia and tibial guidance template. In particular, a tibial template 50 may be used to determine the location and orientation of the tibial tunnel 60. Specifically, an opening 65 within the tibial mold 50 can be designed to establish the position, angle and/or orientation of the tibial tunnel 160. The opening may include optional metal sleeves 68. At least one surface of the tibial template 50 substantially matches the surface of the tibia 75. The template may be matched to a tibial spine 80 wherein the tibial spine can help identify the correct position of the mold and help fix the template in place during the surgical intervention. Of note, the sleeves 30 and 68 may be made of other hard materials, for example, ceramics. The femoral and/or tibial template may be optionally attached to the femoral or tibial articular surface during the procedure, for example using K-wires or screws. The entire template can optionally be made of hard materials, e.g. metal or ceramics.

FIG. 3 shows a top view of the tibial plateau 85. The PCL 86 is seen as are the menisci 87. The original site of ACL attachment 90 is shown. The intended tunnel site 92 may be slightly posterior to the original ACL attachment 90. The template 95 may be placed over the intended graft tunnel 92. The template can include a perimeter slightly greater than the intended tunnel site. Optionally, the template may allow for attachments, linkages, connectors or handles.

Templates may be designed to be compatible with any desired surgical technique. For example, templates may be designed to be compatible with single bundle, double bundle or multiple bundle reconstruction techniques, tibial inlay techniques as well as other approaches. The devices used for such techniques may include specific characteristics to accommodate and facilitate such techniques. For example, in the case of a double bundle technique, a figure-eight aperture or dual apertures may be included to accommodate both bundles.

Referring to FIGS. 4-7, an embodiment of an instrument 100 for accurately and simply placing an ACL tunnel in a tibia during a procedure for the repair or replacement of the ACL is shown.

Figure 6:
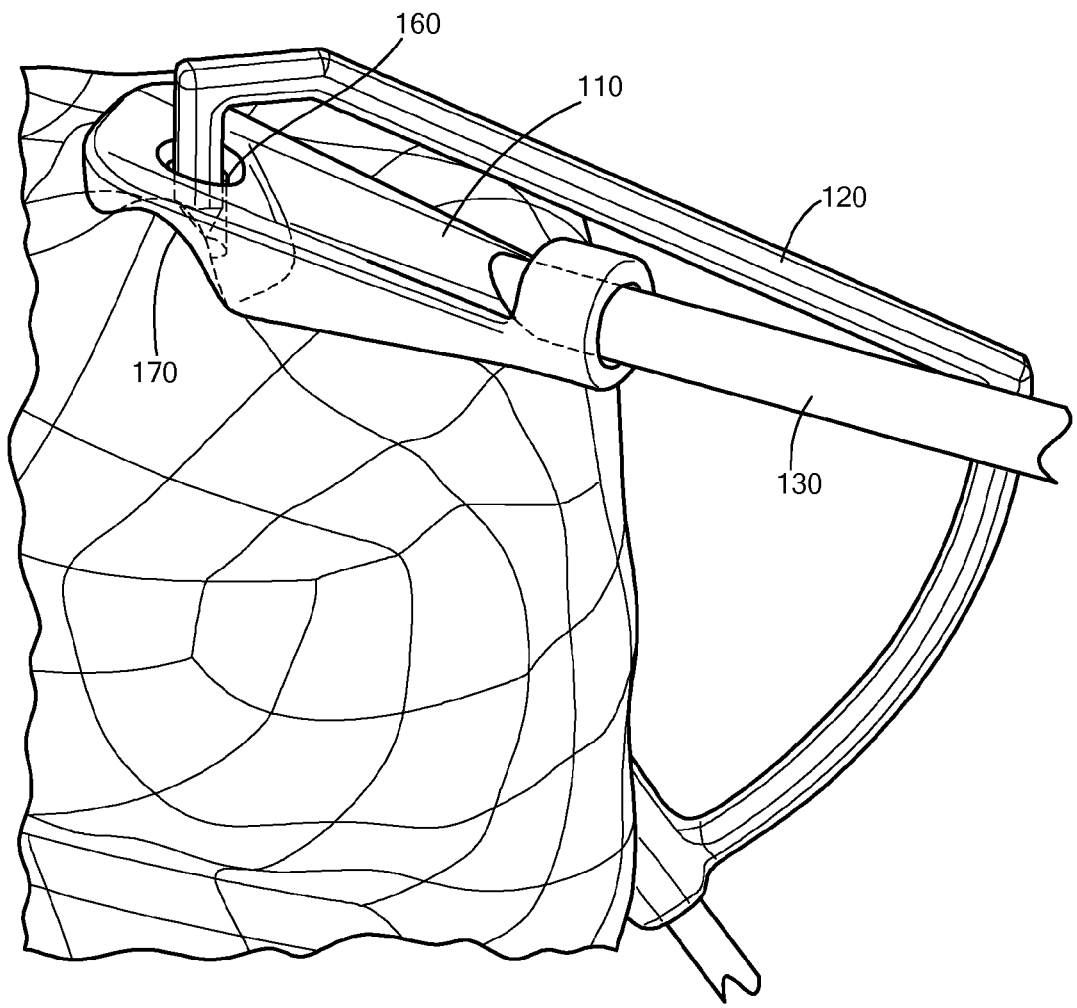
Figure 7:
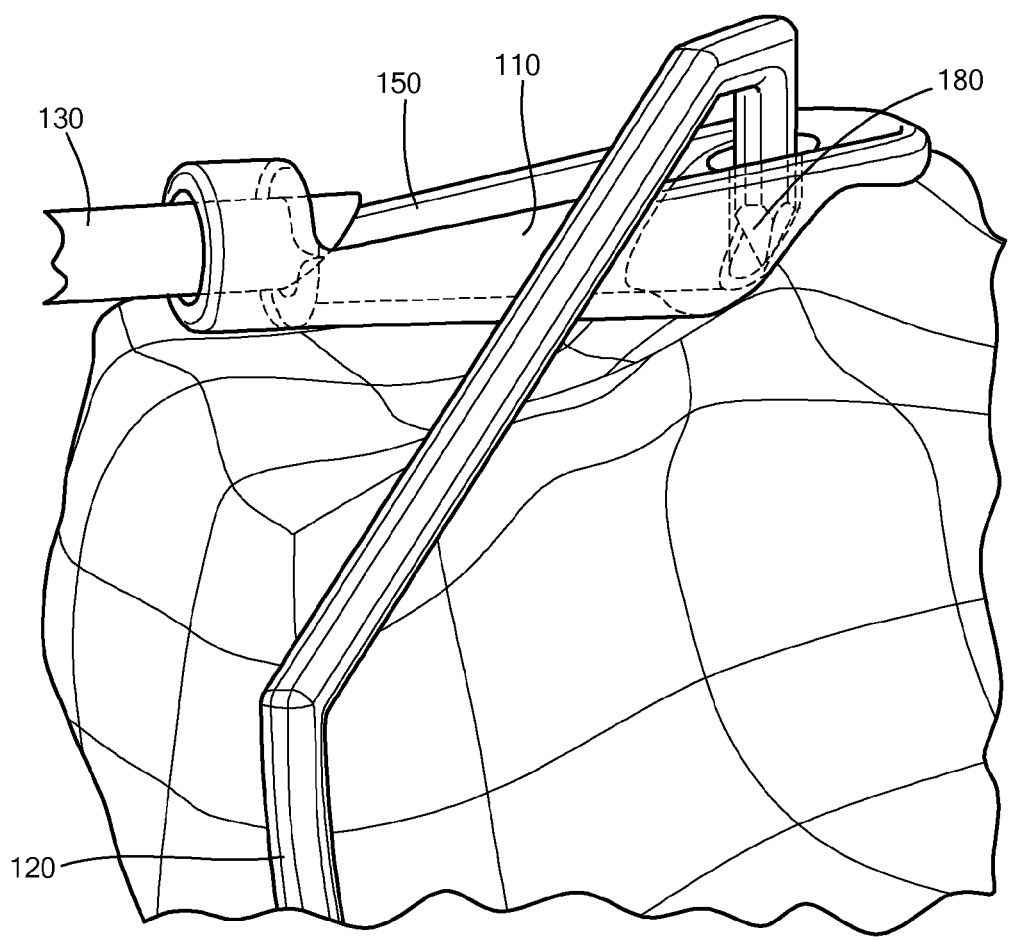

The instrument 100 has two components, a fitting 110 and a guide 120. Fitting 110 is sized for placement at the end of an arthroscope 130 via coupling mechanism 140. Fitting 110 also can include a viewing portal 150, a connection mechanism 160 and/or a registration surface 170. The portal 150 is a hollow passage that allows the arthroscope to view the area of the procedure. Connection mechanism 160 is an opening sized and shaped to register with guide 120 when instrument 100 is fully assembled. Although many embodiments are possible, connection mechanism extends entirely through fitting 110 to form a tunnel, as shown in FIGS. 6-7.

In this embodiment, registration surface 170 is a surface designed as a negative to the specific corresponding portion of the surface of the tibia, preferably in the area of the tibial spine of the patient, such that the surface 170 mates to and registers with the corresponding tibial surface portion. The surface 170 is individualized for a specific patient, and is a substantially negatively matching or conforming surface with the bone surface and conforms to that bone surface. In certain embodiments, registration to the patient's anatomy can be achieved in other ways, for example, by utilizing a set of pins or notches that properly align the instrument by engaging the surface of the bone.

Preferably, the surface 170 is sized to be as small as possible to facilitate placement in the area of the ACL procedure while being sufficiently large to allow an accurate registration with the patient's tibia such that the device accurately positions and orients the location and direction of the tibial tunnel.

Guide 120 includes an aiming tip 180, an arm 190 a pin housing 200, and a registration surface 210. Aiming tip 180 is a pin sized and shaped to mate with connection mechanism 160. Preferably, in this embodiment, the connection between connection mechanism 160 and aiming tip 180 is a close fit such that the connection assists in providing an accurate placement of instrument 100. In some embodiments, the connections can include a threaded coupling mechanism, a snap fit, and/or other mechanism for connection.

Registration surface 210 is located at the end of pin housing 200. Surface 210 is designed to be a negative of a specific corresponding portion of the surface of the tibia of the patient such that the surface 170 substantially negatively conforms (i.e., substantially matches) to and registers with a corresponding tibial surface portion. Like surface 170, surface 210 preferably is sized to be as small as possible to facilitate placement in the area of the ACL procedure while being sufficiently large to allow an accurate registration with the patient's tibia such that the device accurately positions and orients the location and direction of the tibial tunnel.

Arm 190 is sized and shaped to extend around the intervening portion of the head of the tibia, and connects and supports pin housing 200 and fitting 110. Considerable force can be generated by, for example, a surgeon creating (e.g., drilling) an ACL tunnel during such a procedure. Therefore, arm 190 is preferably made of a material capable of withstanding such forces with minimal deformation. Suitable materials for the components of instrument 100 include, for example, cobalt-chromium, titanium, or a sufficiently strong and rigid polymer material.

Pin housing 200 includes an opening 220 that guides a pin and/or drill during the procedure. In some embodiments, a pin or bit can be held captive in pin housing 200.

During the procedure, the instrument can be assembled with surfaces 170 and 210 registered to the corresponding surface portions of the tibia. When fully assembled and properly positioned on the tibia, instrument 100 provides a "catch feel" to the user. Also, when assembled, aiming tip 180 extends through connection mechanism 160 and aiming tip 180 rests on the surface of the bone to define the location of the exit point of the tibial tunnel. The tibial tunnel is created through the head of the tibia exiting the outer surface of the tibia in the vicinity of fitting 110. During this process, the ACL pin is aimed at aiming tip 180.

Many other embodiments are possible. For example, in another embodiment, fitting 110 can be part of, attached to or integrated with aiming tip 180 such that the entire instrument is a single piece, either integrated or assembled from several pieces during the procedure. Although the instrument can include three or more components, preferably the instrument has the same or fewer components as the number of portals used in the surgery, which is typically two.

Figure 8:
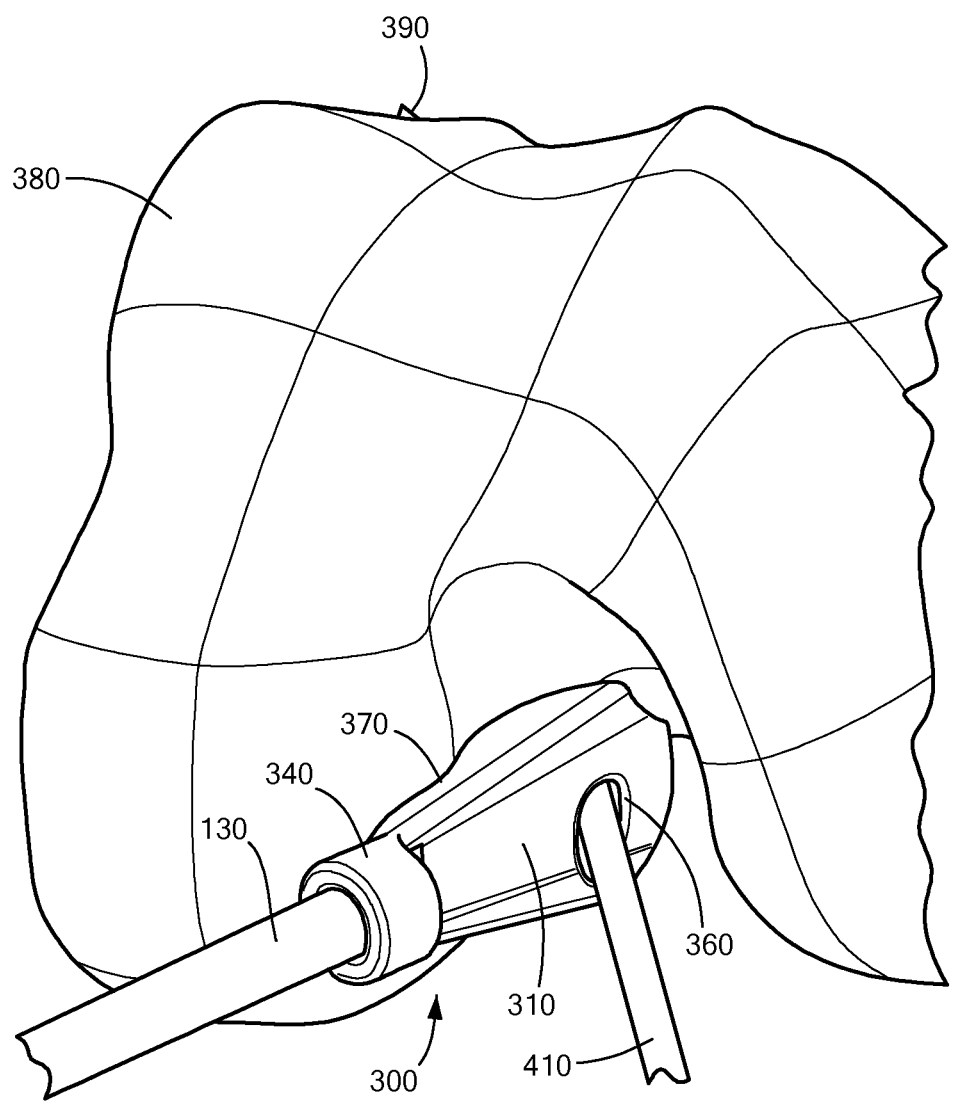
FIG. 8 is a side perspective view of an embodiment of a patient-specific instrument for use in creating (e.g., drilling) a femoral tunnel during an ACL procedure, in accordance with some embodiments of the invention.
Figure 9:
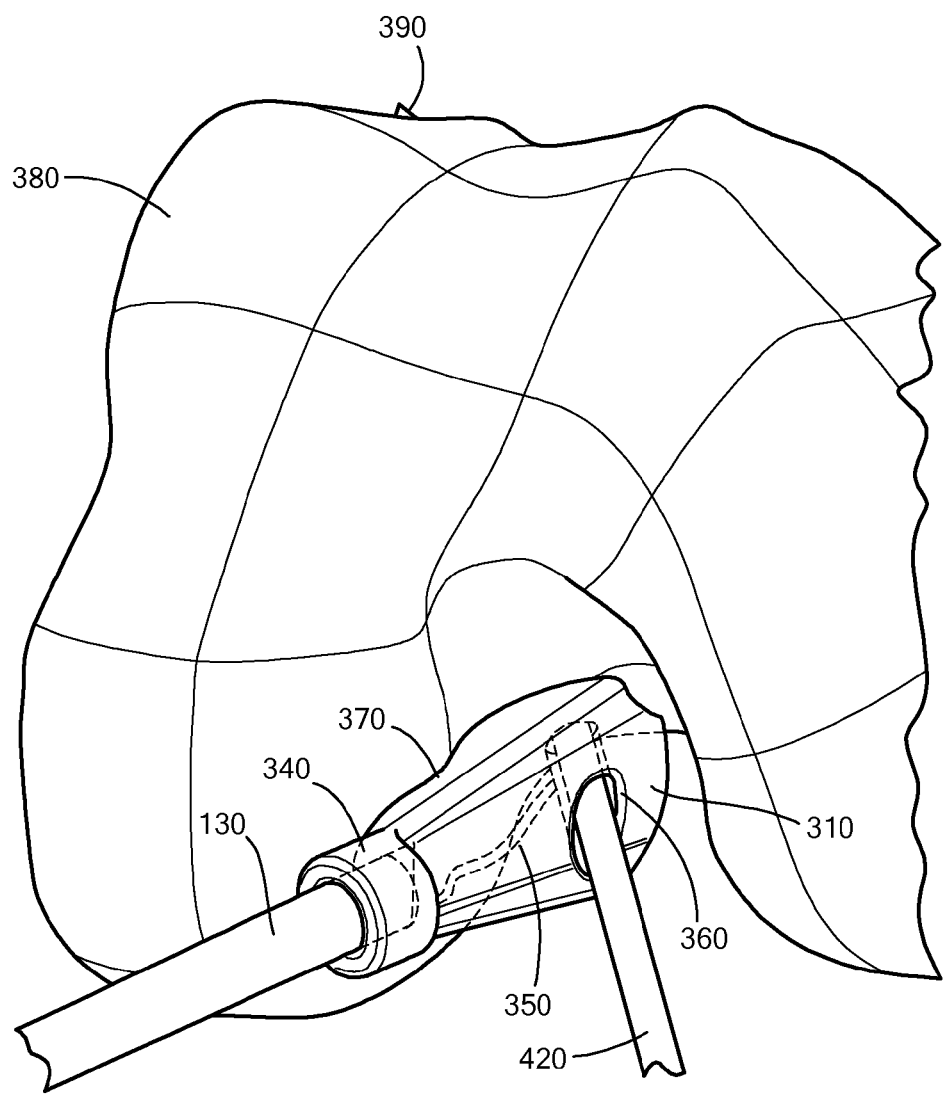
FIG. 9 is a side perspective view of the embodiment shown in FIG. 8, with a fitting component shown in a partially transparent view, in accordance with some embodiments of the invention.

Referring to FIGS. 8-9, a femoral instrument 300 is shown. Femoral instrument 300 preferably is used in the same procedure as tibial instrument 100 to create a tunnel in the distal portion of the patient's femur to secure the opposite end of the ACL graft as the tibial tunnel created with tibial instrument 100. The instrument 300 has one component, a fitting 310. Fitting 310 is sized for placement at the end of an arthroscope 130 via coupling mechanism 340. Fitting 310 also includes a viewing portal 350, a guide mechanism 360 and a registration surface 370 that substantially conforms to (i.e., substantially matches) the corresponding femoral surface (e.g., bone and/or cartilage surface). The portal 350 is a hollow passage that allows the arthroscope to view the area of the procedure.

Figure 10:
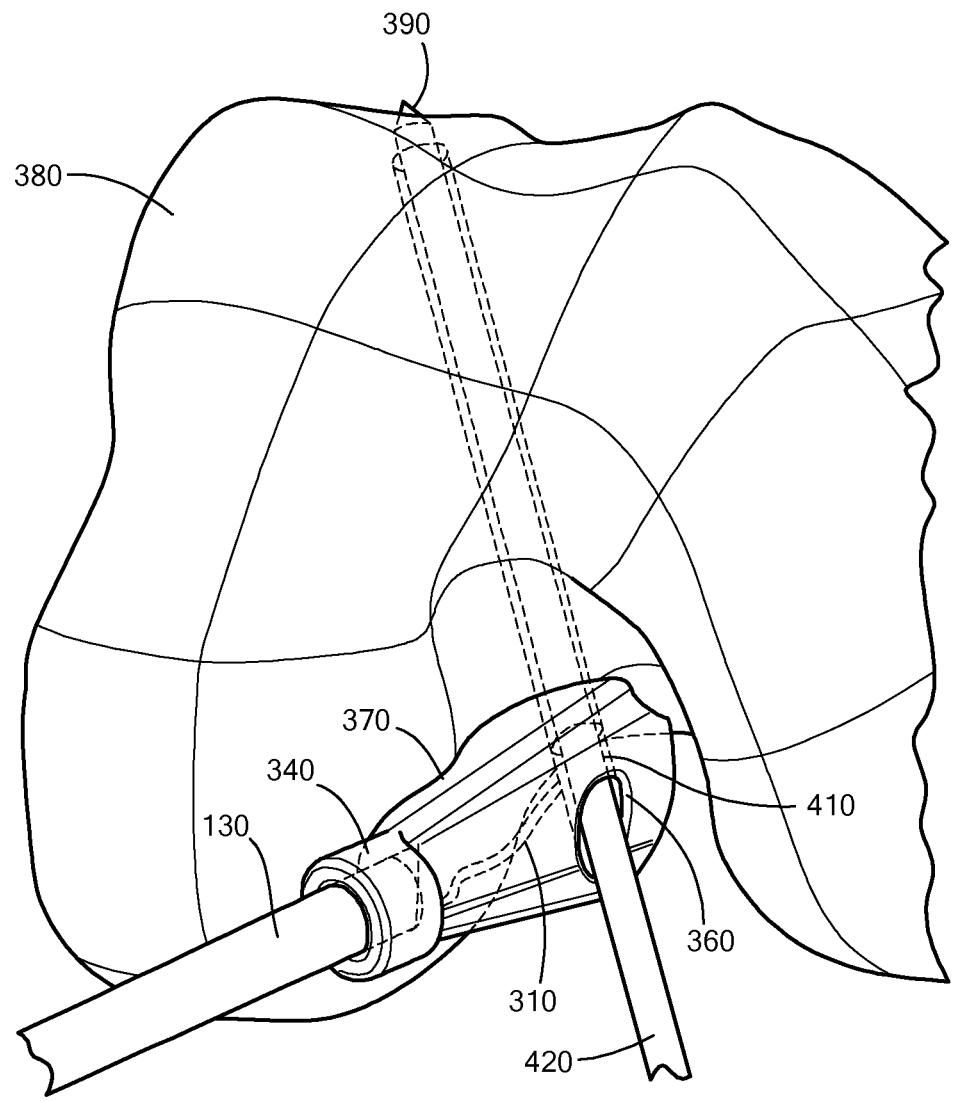
FIG. 10 is a side perspective view of the embodiment shown in FIG. 8, with a fitting component and a femoral condyle shown in a transparent view, in accordance with some embodiments of the invention.

Guide mechanism 360 is an opening sized and shaped to allow the passage of an ACL guide and pin 370 to pass through fitting 310, as shown in FIG. 10. The fit of guide 360 preferably is close enough to allow the guide and pin 420 to pass through with minimal resistance while restraining any significant lateral or rotational movement that would cause the ACL tunnel in the femur to be misaligned. In other embodiments, an ACL guide and pin may be included as part of a femoral instrument.

In this embodiment, registration surface 370 is a surface designed as a negative to the specific corresponding portion of the surface of the femoral condyle, such that the surface 370 mates to and registers with the corresponding femoral surface portion. The surface 370 is individualized for a specific patient, and is a substantially matching surface of the bone surface and conforms to that bone surface. In certain embodiments, registration to the patient's anatomy can be achieved in other way, for example, by utilizing a set of pins, clamps or notches that properly align the instrument by engaging the surface of the bone.

Preferably, the surface 370 is sized to be as small as possible to facilitate placement in the area of the ACL procedure while being sufficiently large to allow an accurate registration with the patient's femur such that the device accurately positions and orients the location and direction of the femoral ACL tunnel. Suitable materials for the components of instrument 300 include, for example, cobalt-chromium, titanium, or a sufficiently strong and rigid polymer material.

Figure 11:
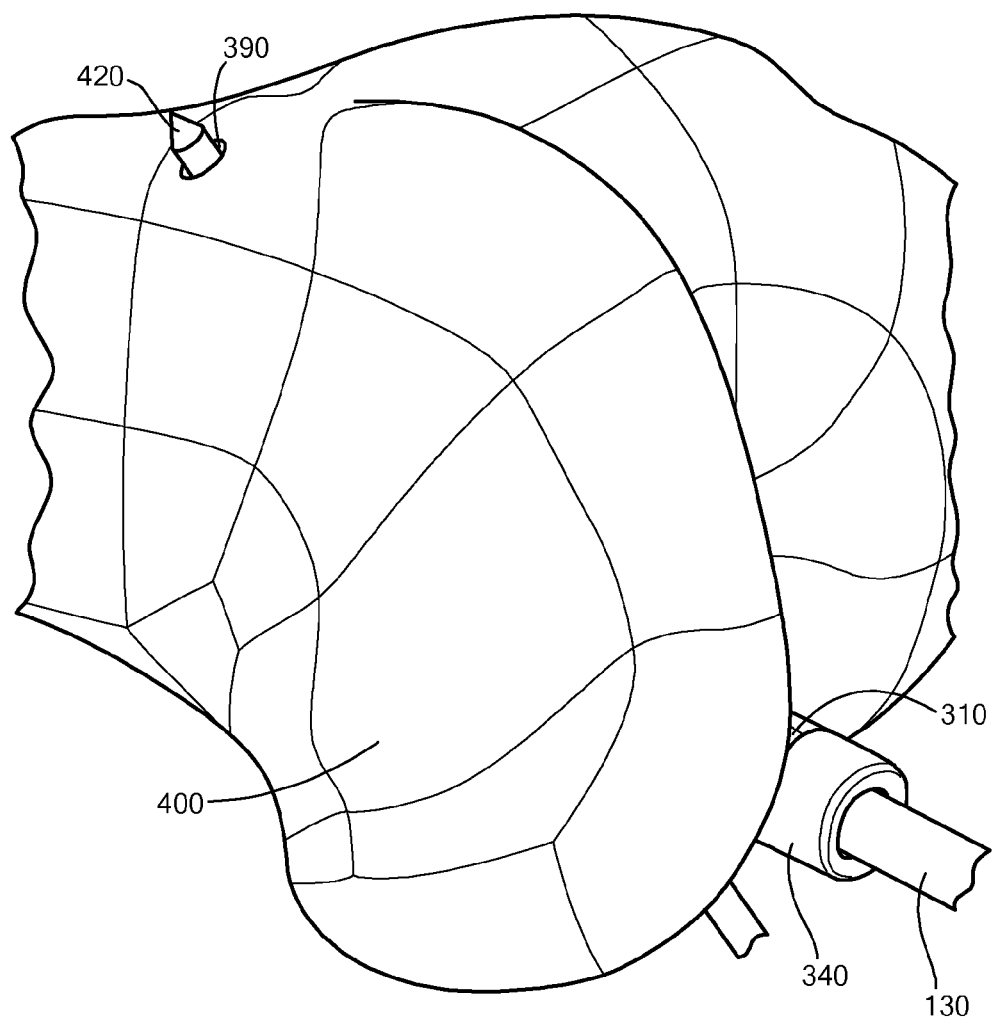
FIG. 11 is a side perspective view of the embodiment shown in FIG. 8, with an exit of a femoral tunnel shown in the femoral condyle, in accordance with some embodiments of the invention.

Referring to FIGS. 10-11, during the procedure, instrument 310 is placed on arthroscope 130 and registration surface 370 is placed against the corresponding surface of the femoral condyle 380. When assembled and properly positioned on the femur, instrument 300 provides a close and secure feel to the user. A femoral tunnel 400, having opening 410, is created through the distal portion of the femur exiting the outer surface of the femur at exit 390.

Many variations on the embodiment features described herein are possible. For example, in certain embodiments, a femoral instrument can include a multi-piece design with multiple (two or more) registration surfaces similar to tibial instrument 100. Alternatively, a tibial instrument can have a single registration surface. However, preferably, the femoral instrument uses a single registration surface to provide a simpler instrument that takes advantage of the ridge on the femoral condyle to provide a secure fit, while the tibial instrument includes multiple registration surfaces to provide a more secure fit over the relatively flatter and less complex geometries typically found on the tibial plateau. Additionally, like the tibial instrument, the femoral instrument can include three or more components, but preferably has no more components than the number of portals involved in the procedure.

In one embodiment, an instrument similar to instrument 100 can include a fitting that additionally includes a tunnel-shaped opening that aligned along the same axis as the guide on the side of the tibia. Thus, rather than aiming a pin at an aiming tip on the tibial plateau, the pin can be moved along the axis of alignment and pass through both the guide opening and the opening in the fitting in one motion. Such embodiments can be used with the tibia and femur as well as with single and multi-bundle embodiments in the knee or other joints. Additionally, such embodiments can include two unattached guides or, alternatively, can include an arm connecting the two guides to add additional registration of the orientation of the pin openings as well as additional stability during the procedure.

In still other embodiments, the femoral and tibial tunnels can be created using a single instrument that provides for an alignment of both the tibial and femoral tunnel locations such that the tunnels can be created using one cut along a common axis. Preferably, in this and other embodiments, the tunnels is created in a manner and orientation that reduces and/or eliminates the eccentricity of the tunnel openings that open into the joint cavity, such that the tunnel is circular or more circular in shape. Among other things, this helps reduce wear on the ACL graft at the edges of the openings, and is thought to be the geometry preferred by most doctors performing such procedures.

The above embodiments discussed in conjunction with FIGS. 4-11 involve a single-bundle technique. One potential drawback to the single-bundle technique is that the procedure may not reproduce the patient's native anatomy. First, the procedure does not reproduce the pre-existing ACL, which is formed of two bundles, the anteromedial (AM) and posterolateral (PL) bundles, each of which attaches in slightly different locations on the tibia and femur. Additionally, the single-bundle method may result in a tunnel mismatch. Instead of connecting the tibial AM site to femoral AM site and tibial PL site to femoral PL site, it may produce some kind of mismatch by connecting tibial PL site (B) to femoral AM site (A), or tibial PL site (B) to a high AM site (high).

Accordingly, in some embodiments, this mismatch is avoided because the precise location of the patient's AM and PL connections can be determined and incorporated into the instrumentation. Such embodiments including, without limitation, those discussed in conjunction with FIGS. 4-11, can improve the single-bundle ACL reconstruction technique by more closely matching the locations and orientations of the native ACL being reconstructed.

Other embodiments can be used in an ACL procedure to employ a double bundle technique, which can closely replicate the patient's native anatomy both by accommodating two reconstructed ACL bundles and by providing a closer match to the native alignment and orientation of the patient's native ACL AM and PL bundles than a doctor can do with existing methods and devices. One such embodiment is shown with reference to FIGS. 12-15 below.

Figure 12:
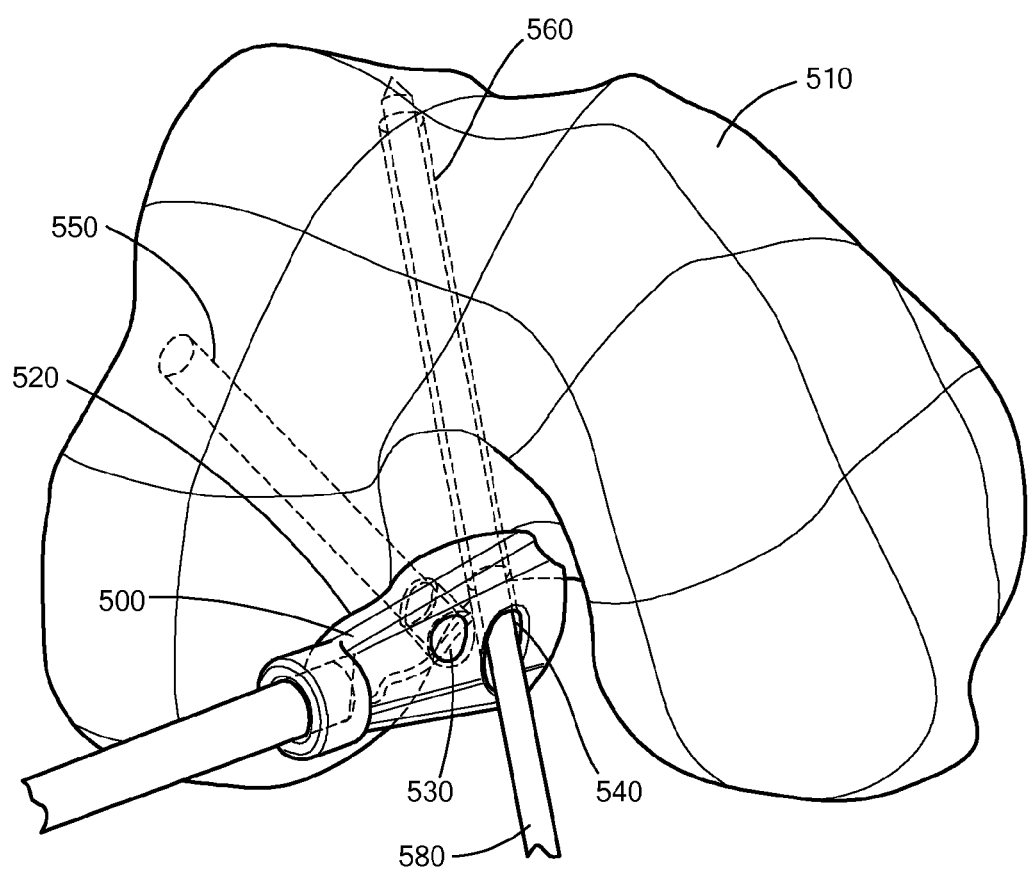
FIGS. 12-13 are side perspective partially transparent views (viewed axially from a distal end of a femur) of an embodiment of a patient-specific instrument for use in creating femoral tunnels during a double-bundle ACL procedure, in accordance with some embodiments of the invention.
Figure 13:
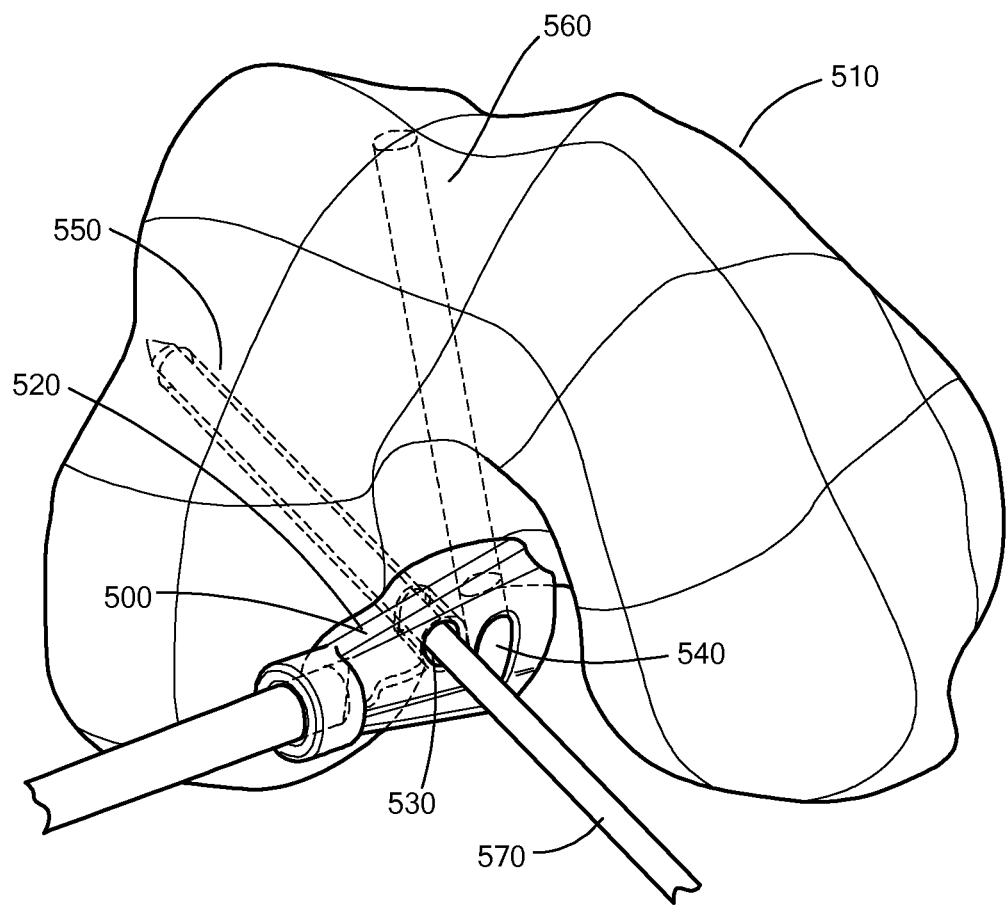

In FIGS. 12-13, a femoral instrument 500 for use in a double-bundle ACL reconstruction procedure is shown at the distal end of a femur 510. The instrument 500 is similar to instrument 300 discussed above. Here, instrument 500 includes a conforming patient-specific surface 520 that positions and aligns instrument 500. Instrument 500 also includes two openings 530 and 540 for creating the two femoral tunnels 550 and 560 used to secure a reconstructed double-bundle ACL. In FIG. 12, the first tunnel 550 is created using pin 570 (or other appropriate device such as a drill). The second tunnel 560 is created using pin 580, as shown in FIG. 13.

Figure 14:
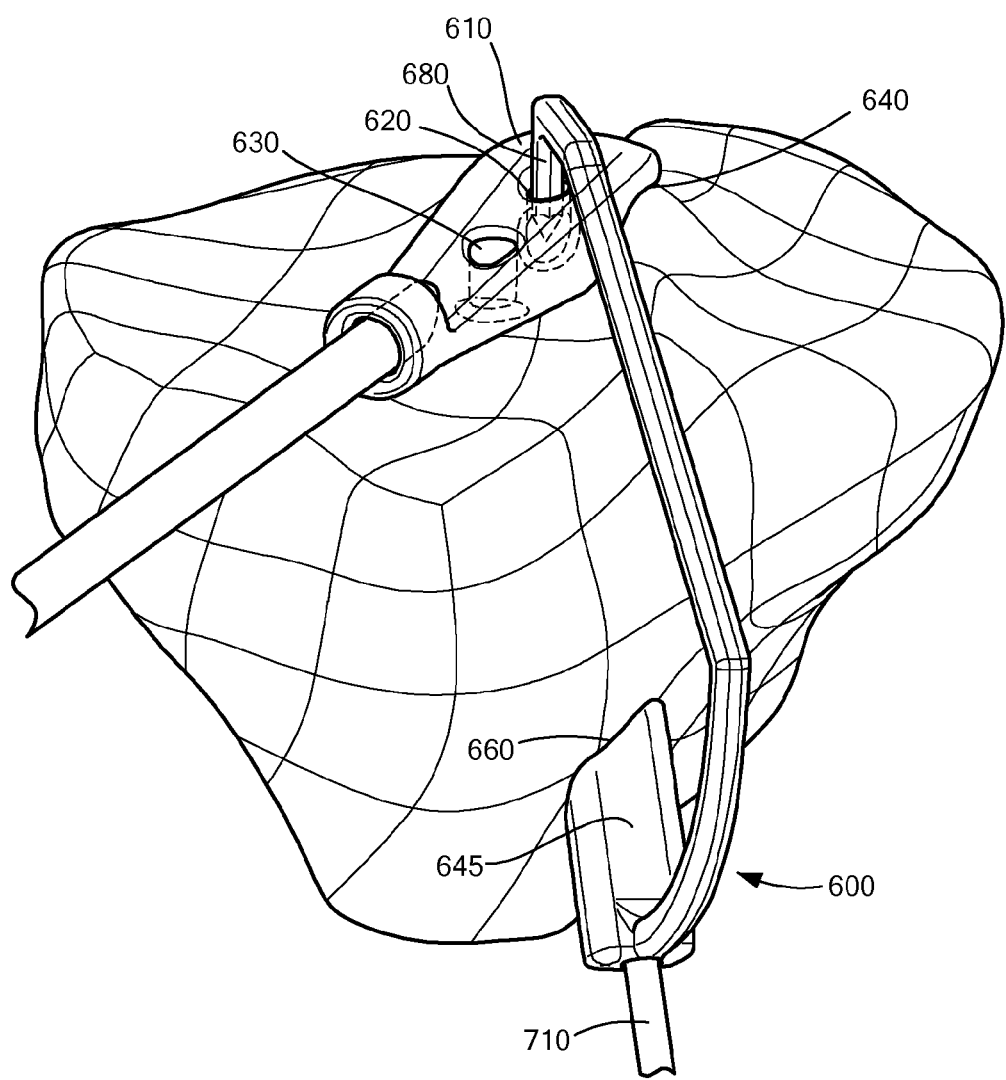
FIGS. 14-15 are side perspective partially transparent views of an embodiment of a patient-specific instrument for use in creating tibial tunnels during a double-bundle ACL procedure, in accordance with some embodiments of the invention.
Figure 15:
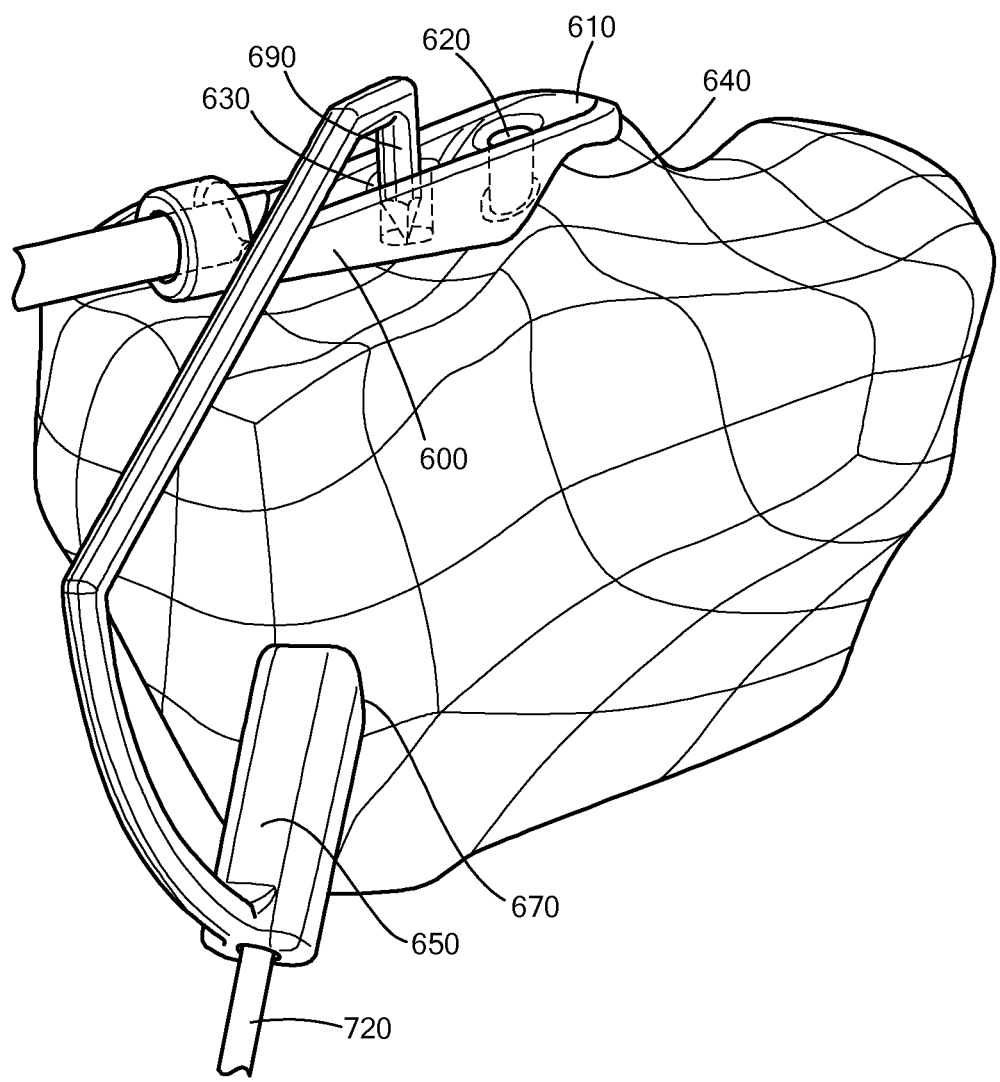

Referring to FIGS. 14-15, a tibial instrument 600 can be used in conjunction with (or separate from) femoral instrument 500 to create two tibial tunnels during a double-bundle ACL reconstruction procedure. (Alternatively, in an alternate embodiment, a single tibial tunnel can be created with the two femoral tunnels, provided the single tunnel is properly sized to include both ACL bundles.) Instrument 600 has a structure and function similar to tibial instrument 100 discussed above, but, in addition to tip 610 with a registration surface 640, instrument 600 also has two guide components 645 and 650. Each guide component has a unique registration surface 660 and 670 respectively and as well as aiming tips 680 and 690. Additionally, tip 610 includes two openings 620 and 630 for creating two tibial tunnels during the procedure.

During the procedure, the first guide component 645 is optionally attached to tip 610 by placing aiming tip 680 in opening 620. Patient-specific registration surfaces 660 and 700 are registered to the corresponding surface of the tibia as shown. The length, shape and/or orientation of instrument 600 can be adapted based on imaging data, or can be adjusted intraoperatively so that guide components 645 and 650 can be simultaneously aligned with openings 620 and 630 respectively. The first tunnel is then created using pin 710 (or other appropriate device such as a drill). Then, the first guide component 640 is removed and the second guide component 650 is attached to tip 610 by placing aiming tip 690 in opening 630. Patient-specific registration surfaces 670 and 640 are registered to the corresponding surface of the tibia as shown. The second tunnel is then created using pin 720. Alternatively, either or both of the femoral instrument 500 and the tibial instrument tip 600 can each include a single opening to create one tunnel, and a second companion component can be included with a differently oriented opening to create the second tunnel. In still other embodiments, one tibial tunnel can be created with two femoral tunnels or vice versa.

Figure 16:
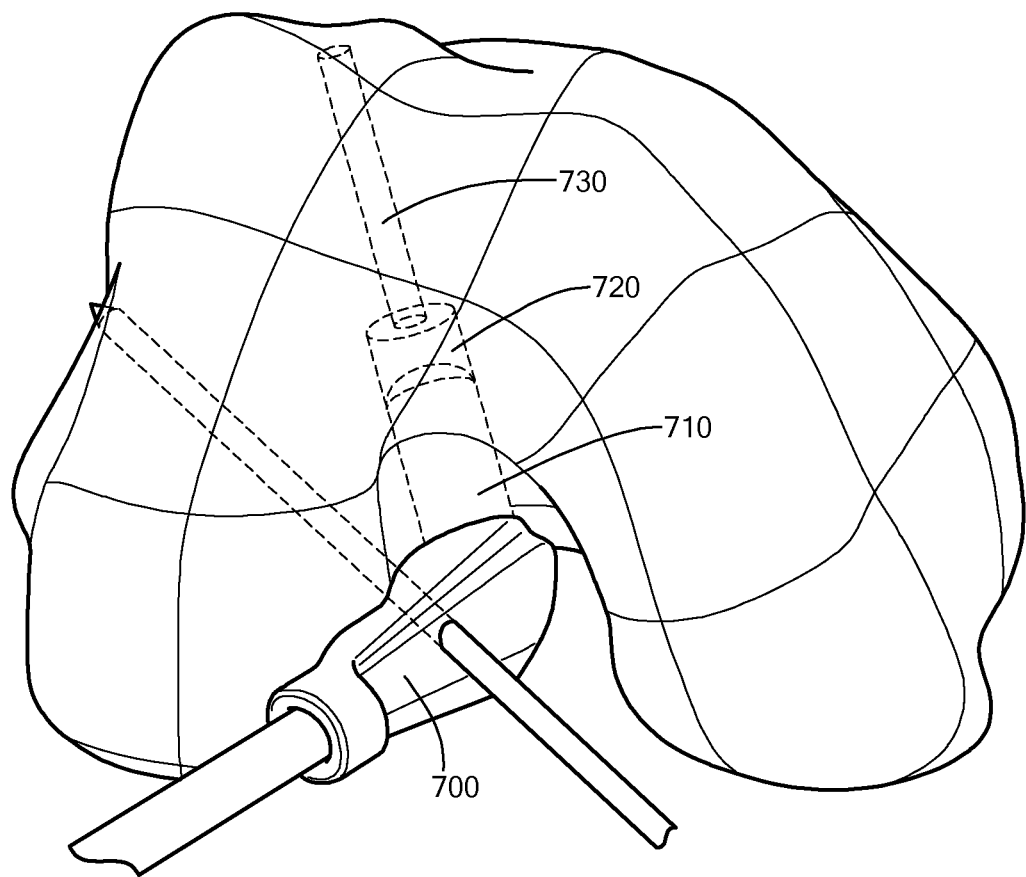
FIG. 16 is a side perspective partially transparent view (viewed axially from a distal end of a femur) of an alternate embodiment of a patient-specific instrument for use in creating femoral tunnels during a double-bundle ACL procedure, in accordance with some embodiments of the invention.
Figure 17:
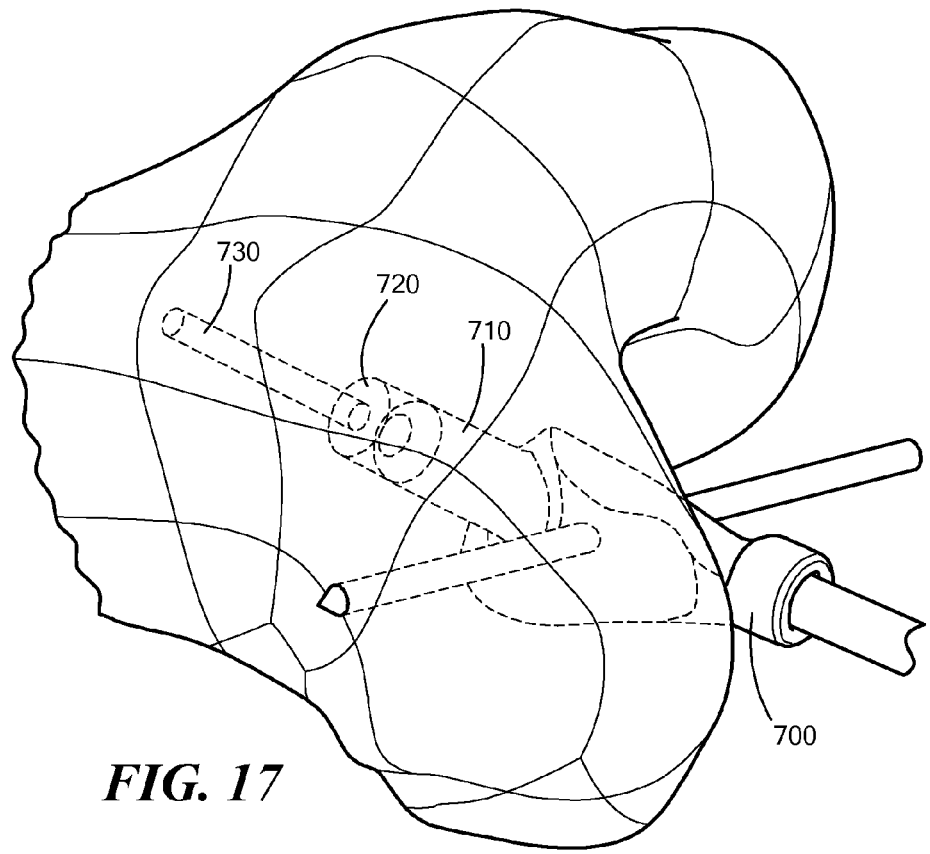
FIG. 17 is an alternate view of the device shown in FIG. 16, in accordance with some embodiments of the invention.

Referring to FIGS. 16-17, an alternate embodiment of a femoral instrument 700 for performing a double bundle ACL reconstruction is shown. Instrument 700 functions in a manner similar to instrument 500 discussed above. However, instrument 700 additionally includes a larger bore section 710 that provides for an enlarged section 720 of tunnel 730 that has a larger diameter than the remainder of tunnel 730 to accommodate a larger ACL graft. In this embodiment, the larger bore section 710 can optionally be formed by drilling out additional bone after the narrower tunnel 720 is initially formed.

In other embodiments, the tunnels can be created by using pins placed in a first tunnel to create additional referencing and stability for the drilling of later tunnels, either on the same portion of the bone, e.g., first and second femoral tunnels, or on different portions of bone, e.g., first tibial tunnel and first femoral tunnel, second femoral tunnel and first tibial tunnel, first and second tibial tunnels and first and/or second femoral tunnels, or another combination of tunnels.

While the embodiments described above in conjunction with FIGS. 12-15 use the native insertion sites for the AM and PL ACL bundles, other embodiments are possible, including embodiments that allow the location and positioning of the sites during the ACL procedure, the adjustment of the location and positioning of the sites during the ACL procedure, the location and positioning of the anatomical attachment sites automatically prior to the procedure, or the location and positioning of optimal or more optimized attachment locations to produce better kinematics and/or stability than existed in a patient prior to the procedure, especially in patient's that exhibit joint disease, such as, without limitation, osteoarthritis or degradation of the existing ACL and/or the associated tissue.

Prior to a procedure, including both ACL and other types of surgery, the remnants of a damaged ligament or other soft tissue can be removed. However, in the case of ACL and other procedures, many doctors prefer to leave the tissue to help locate and position the tunnel openings. In such cases the instrument can be designed to avoid the remnants of the tissue by customizing the instrument to the patient or including such features in a standard design.

In various embodiments, the registration surface that conform to (i.e., substantially matches) a corresponding surface of the patient's anatomy can be designed to substantially match a surface of bone (including, without limitation, cortical and/or subchondral bone), cartilage, other soft tissues or combinations of tissue.

In still other embodiments, the imaging studies created to design the instrumentation can also be used to plan a procedure. For example, a graft can be selected, the length of the graft determined, the position of the graft determined, the orientation, sizing and positioning of the tunnels can be determined. Further, the procedure and the instruments can be designed to include doctor input to account for specific circumstances of the patient and/or procedure as well as doctor preferences for techniques and device features. Additionally, the instrumentation can be designed to allow the doctor to make adjustments during the surgery. Various geometrical aspects of the instruments can also be controlled, such as the angle and spacing between tunnels to ensure sufficient bone stock lies between each tunnel. Variations of the procedures can also include placing the instrumentation via different portals and or creating tunnels via different available portals.

The placement of the location of the AM and PL portions of the double bundle ACL graft can be determined using the patient's existing anatomical landmarks and/or combinations of landmarks. For example, the bony ridge between the attachment sites for the native AM and PL portions of the patient's ACL can be located using a CT scan, and can additionally be used in combination with one or more average offset values, for example from a ridge of the trochlear groove to one or both of the AM and PL attachment sites.

In still other embodiments, the instruments can be placed on the arm of a robot to help register the position of the robot during surgery, which may significantly reduce the amount of preparation time for robot-assisted procedures.

1.3 PCL Treatment

Like ACL repair, treatment for the management of posterior cruciate ligament (PCL) injuries continues to evolve.

Currently, the selection of a treatment protocol depends on many factors. In some embodiments, selecting the best option takes both patient and injury factors into consideration. While the location, timing, severity, and extent of associated injuries can be important prognostic factors, the patient's age, occupation, health, gender and expectations can play an equally important role in the decision-making process. Currently, many acute, isolated partial PCL injuries (grades I and II) do not beget surgical intervention. The likely benign course of these injuries is related to the remaining integrity both of secondary restraints and of various portions of the PCL. Furthermore, these partial tears have been shown to have a strong propensity to heal. Chronic residual posterior laxity may occur if these injuries are not treated appropriately, causing the ligament to heal in an elongated position. Therefore, the initial treatment of partial PCL injuries can include protected weight bearing, the use of a knee immobilizer or brace with drop-lock hinges, and/or a quadriceps and triceps rehabilitation program to counteract posterior tibial subluxation. The nonoperative course for isolated, complete tears of the PCL (grade III) does not have a high success rate. Unfortunately, many of these injuries do not heal, and over time these patients can develop symptoms secondary to increased shear stresses to the articular cartilage, especially in the medial and patellofemoral compartments. Thus, surgery frequently is the recommended option for these patients, especially if they continue to be symptomatic despite maximizing physical therapy.

Current PCL reconstructive techniques continue to evolve but often include: 1. identifying and treating associated pathology; 2. minimizing the risk of neurovascular injury; 3. selecting, placing, appropriately tensioning and rigidly fixing an adequately strong graft; and 4. preparing for prolonged rehabilitation.

1.3.1 Repair vs. Reconstruction

The decision to repair or reconstruct a torn ligament depends on a number of factors. MRI is particularly helpful in determining which structures are repairable and which can be reconstructed. In general, repairs are not as strong as reconstructions, and modification of the postoperative protocols are often designed reflect this difference. Unfortunately, as with ACL injuries, primary repair of midsubstance PCL tears has not been consistently successful. The exception is cases of PCL bony or ligament insertion avulsions, where repair of these injuries typically results in a favorable outcome. Several surgical approaches can be utilized depending on other associated ligament and meniscal injuries that may require treatment and include the posteromedial, posterolateral, and posterior approach to the knee as well as all arthroscopic techniques. In addition, various fixation methods have been described and depend on the size of the bony fragment. For large avulsion fragments, AO screws can be used, whereas smaller fragments can be stabilized with Kirschner wires or tension band wiring, or by suture repair through drill holes.

1.3.2 Techniques of Reconstruction

Several different methods have been developed for PCL repair or reconstruction. Most surgeons now agree that restoration of normal anatomy yields the best potential for consistent results after PCL reconstruction. Numerous variables exist, including graft choice, type of fixation, tunnel placement, as well as inlay versus tibial tunnel techniques. The two most commonly employed reconstructive techniques are the transtibial tunnel and the tibial inlay techniques. Moreover, some studies have shown that a double-bundle construct may have the best chance of reproducing the biomechanics of the PCL in vitro; however, clinical studies have not confirmed the improved results of this technique over single-bundle reconstructions in vivo.

1.3.3 Graft Choices and Fixation Methods

A variety of tissues have been used for knee reconstructions. Autologous tissues include patellar, hamstring, or quadriceps tendon. Achilles tendon, patellar tendon, and tibialis anterior tendon are the most commonly used allograft tissues. Several studies have documented by arthroscopy and histologic methods that the transplanted allograft tendons revascularize, undergo cellular repopulation and reach maturity just as autograft tissue does, although this process may take longer with allograft tissue. An Achilles tendon allograft is often preferred because of its high tensile strength, shorter operating time, ease of passage, and lack of donor-site morbidity in an already compromised knee. Additional benefits include its exceptional size and length and bony attachment at one end, making it quite versatile when compared to other graft options. Multiple methods of fixation also exist, including metal and bio-interference screws, buttons, cortical screws and soft tissue washers, or staples. Use of a screw and soft tissue washer is preferred when securing soft tissue to bone in most instances, as this has been shown to be the most stable fixation.

1.3.4 Tunnel Placement and Graft Tensioning

Biomechanical studies support reconstruction of the anterolateral bundle when performing a single-bundle technique. Anterior placement of the femoral tunnel in the anatomic footprint has been shown to restore normal knee laxity better than isometric graft placement. Similar to ACL surgery, placement of the osseous tunnels can be important to the success of the procedure. Variations in tibial tunnel placement can affect graft behavior to a lesser degree than femoral tunnel placement variations. Furthermore, the position in which non isometric graft is tensioned and fixed can have a significant effect on knee mechanics.

1.3.5 Single-Bundle Reconstruction

The single-bundle technique was developed to reconstruct the anterolateral bundle because of its larger size and greater biomechanical properties when compared with the posteromedial bundle. In an attempt to place the graft in the anatomic position of the native anterolateral bundle, single tibial and femoral tunnels can be utilized. Reproduction of the normal anatomy may be the ideal location with anterior placement of the tunnel in the anatomic anterolateral bundle footprint of the femur. Good results have been reported with this approach along with tensioning of the graft in 90 degrees of knee flexion with an anterior drawer force.

Regarding tibial tunnel placement, it has been shown that transtibial drilling techniques from the anteromedial tibia can create an unwanted tunnel curve. Techniques have been developed to limit this graft angulation using a posterolateral tibial tunnel as well as the tibial inlay technique described below.

1.3.6 Double-Bundle Reconstruction

Double-bundle reconstruction techniques have been introduced in an attempt to reproduce more accurately the complex functional anatomy of the PCL. It has been shown in cadaver studies that double-bundle PCL reconstruction may more closely restore normal knee biomechanics throughout its full range of motion. While traditional single-bundle reconstruction restores knee biomechanics at mid- to high knee flexion angles, there can be residual laxity when the knee is near full extension. Biomechanical studies have shown the addition of the posteromedial bundle reduced posterior tibial translation in knee flexion, as well as extension, suggesting that this bundle can serve an important role throughout knee flexion. Although technically challenging, double-bundle reconstruction has become a preferred surgical technique in chronic PCL deficiency because of its improved restoration of normal knee mechanics.

1.3.7 Tibial Inlay

The tibial inlay technique was initially introduced to circumvent the issues of bone plug passage through the long tibial tunnel and potential abrasion at the posterior tibial exit point. It can also facilitate protection of the neurovascular structures. Utilization of the posterior approach to the tibial insertion of the PCL as can simplify the posterior exposure. The technique has been utilized most commonly with patella tendon autograft, but recently it has been described in use with a double-bundle Achilles allograft.

1.3.8 Combined Injuries

The combined PCL-(posterolateral structures) PLS injury is one of the most complicated knee injury patterns that an orthopedic surgeon may experience. When both the PCL and PLS are ruptured, substantial posterior translation, external rotation, and varus opening may all be present at differing angles of knee flexion. This combination creates a complex surgical dilemma that usually necessitates the surgeon having more than one surgical plan. Many techniques of reconstruction have been devised, including arcuate ligament advancement, biceps tenodesis, and popliteofibular ligament reconstruction with allograft or autograft tissue. Chronic cases of posterolateral instability demonstrate tissue redundancy and excessive scarring posterior to the LCL, making identification of the particular structures of the popliteus complex difficult. Therefore, the timing of surgical treatment of the injured PLS is significant, with acute repairs consistently giving more favorable results than reconstruction of chronic injuries. Chronic PCL injuries involving the PLS are even more surgically challenging. If an injury to the PLS is ignored or goes unrecognized, repair or reconstruction of other ligaments may have a significant risk of failure due to chronic repetitive stretching of the reconstruction. Surgical treatment of PLS injuries in the chronic injury setting is centered on reconstruction rather that repair of deficient structures. Anatomic reconstruction of the popliteofibular ligament is preferred and, if needed, the LCL. If varus malalignment or a lateral thrust exists, a proximal tibial osteotomy may be performed to correct the alignment. Although the osteotomy may be performed in conjunction with the PLS reconstruction, the operation may be staged since the osteotomy alone may alleviate the patient's symptoms, thereby avoiding further surgical intervention.

1.3.9 Complications

Failure to recognize and appropriately treat associated ligament injuries are the most frequent problems encountered in PCL surgery. Careful examination both prior to surgery and in the operating room, with attention to both MRI and arthroscopic findings, can improve identification of all injured structures. For many patients, successful results depend on repair and/or reconstruction of all torn structures. Alternatively or in addition, injury to a patient's artery, vein or the tibial nerve during surgery are potentially devastating complications. Injury can occur at the time of guide pin passage, or while reaming. In some embodiments described herein, PCL tibial guides are designed with protective aiming arms to mitigate the likelihood of such an injury during surgery. Drilling through the posterior cortex of the tibial tunnel by hand can be an important safety measure for the transtibial tunnel technique. A posteromedial safety incision is another strategy that can reduce this risk. The tibial inlay technique, by eliminating the transtibial tunnel, is another way to limit the risk of neurovascular injury.

1.4 Patient-Specific Tools and Methods for PCL Treatment

All of the embodiments described above in the context of ACL repair may also be applied to PCL repair, as well as to the repair of other ligaments or tendons.

For PCL repair, guidance templates may be designed for single as well as double bundle surgical techniques. With the single bundle surgical technique, a guidance template may be created with a position, orientation and/or shape of the template or associated reference points or guide apertures for surgical instruments that help create a femoral tunnel in a desired location, for example, in the location of the anatomic origin of the ligament. Alternatively, the template and any related reference points or guide apertures or linkages may be designed and placed so that an anterior placement of the femoral tunnel in the anatomic footprint is performed. A more anterior placement of the femoral tunnel can, optionally, restore normal knee laxity better than isometric graft placement. The guidance templates may be designed so that optimal tension is achieved not only in knee extension but also in knee flexion, particularly at ninety degrees of knee flexion. Thus, the origin and the insertion of the PCL may be identified pre-operatively on the scan, either by identifying residual fiber bundles or by identifying the underlying anatomic landmarks. The distance between the origin and the insertion may thus be determined in the extension and can be simulated (e.g., virtually simulated using a patient-specific model of the patient's joint) for different flexion degrees or other articular positions. Kinematic modeling and simulation as well as finite element modeling can be performed for further optimization, as outlined above for ACL repair where similar principles apply. Femoral and tibial tunnel placement and orientation may then be optimized in order to achieve an isometric or near isometric ligament placement. Intraoperative adjustments are feasible as described in the foregoing embodiments.

A guidance template may also be designed both on the femoral as well as on the tibial side using double bundle reconstruction techniques. With double bundle reconstruction techniques, the femoral or tibial template can include or incorporate links or can have attachable linkages so that a femoral tunnel can be created and cross referenced with a tibial tunnel, or a tibial tunnel can be created and cross referenced to a femoral tunnel.

As described for the ACL, the templates may include stops for drills and reaming devices or other surgical instruments, for example, to protect popliteal neurovascular structures. The templates may include extenders or flanges to serve as tissue retractors as well as tissue protectors.

As previously stated, guidance templates are applicable to any type of ligament or tendon repair, not only ACL and PCL repair, and can provide reproducible, simple intraoperative location of intended attachment sites or tunnels. The size, shape, orientation and position of the guidance templates may be individualized and optimized for articular anatomy, as well as the biomechanical situation, and may incorporate not only a shape that conforms to a corresponding articular shape on the patient's anatomy, but also can include patient-specific anatomic lines, anatomic planes, biomechanical lines or biomechanical planes (e.g., marked on the templates), as well as portions or all of the shape of devices or anchors or instruments to be implanted or used during implantation or used during surgical repair of a ligament or tendon tear. Aside from optimization of the anatomic placement, the techniques described herein also allow for kinematic modeling and simulation, finite element modeling, all optionally integrated with the patient's imaging data, as well as intraoperative assessment of graft function and related adjustments.

Figure 18:
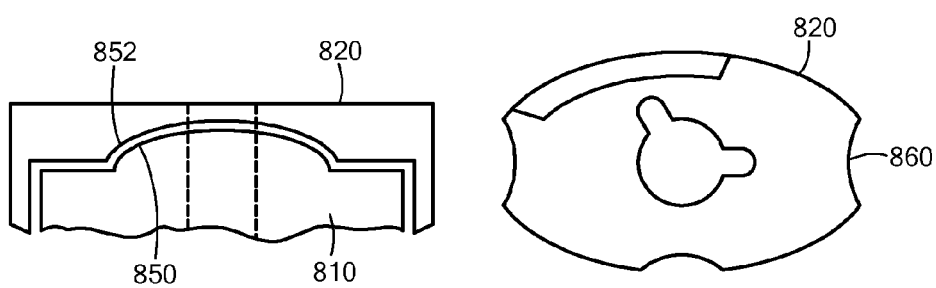
FIGS. 18-19 illustrate a template designed to avoid impingement on the cruciate ligaments during use, in accordance with some embodiments of the invention.
Figure 19:
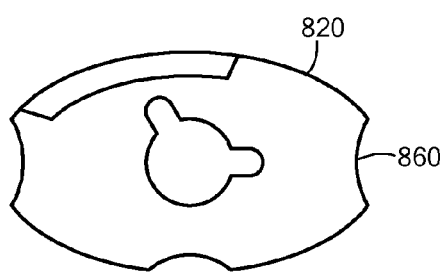

FIGS. 18 and 19 illustrate an alternative design of a cutting block 820 that provides additional structures 860 to protect, for example the cruciate ligaments, from being cut during a surgical procedure. These additional structures can be in the form of indented guides 860, as shown in FIG. 19 or other suitable structures. As shown in FIG. 18, a device can include an inner mold 810 configured such that the upper surface forms a convex dome 850 that fits with a concave well 852 provided on the interior surface of the cutting block 820.

In an alternate embodiment, the various components used can be small enough to be inserted via an endoscope, arthroscopy portal or other device that provides a passage to access the joint. Additionally, in some embodiments, the tools and devices can be designed in segments or pieces, preferably small segments or pieces, which can be assembled at the location of the surgical procedure in the body once inserted into the body. Such devices may have locking or other mechanisms (such as mechanical or magnetic couplings) that allow the device to be assembled.

In another embodiment, a template for the placement of a distal tunnel can be dispatched via a proximal tunnel that has already been created during the procedure. For example, if a tibial tunnel has been created, a template can be placed to create a femoral tunnel via the tibial tunnel. As another example, the reverse situation is also possible. If a femoral tunnel has been created, a template can be placed to create a tibial tunnel via the femoral tunnel. The first tunnel can be placed beginning either from within the joint space moving outward or from outside the joint space moving inward toward the opposing articular surface.

This concept is applicable towards any type of ligament repair, not only ACL and PCL. The tools and devices or segments and pieces may be inserted through a bone tunnel that extends into the joint.

Such a device may preferably be constructed of several small components that are dispatched through a portal or incision or a bone tunnel and assembled at the location of the distal femoral articular surface. Various embodiments can include a multi-component device that is assembled to register with (e.g., have a surface that substantially matches) a portion of one articular surface, a multi-component device that is assembled to register with a portion of one articular surface and is linked to a tunnel opposing the articular surface to which the device registers, a multi-component device that is assembled to register with a portion of both articular surfaces, and a multi-component device that is assembled to register with a portion of both articular surfaces and is linked to the tunnel opposing the articular surface to which the device registers. Other embodiments are possible.

The template or components thereof can also be of expandable design. Such expandable designs can optionally utilize Nitinol or other "memory-like" materials. Preferably, the template or tool or device and components can be small in shape or cross-section prior to insertion and at the time of insertion. Once inserted, the template or tool or device and components can expand. The expansion can be active, e.g., in the case of Nitinol, or passive, e.g., via secondary devices that help expand the device or tool. Moreover, one or more surface of the device can be patient matched, for example using the imaging data. Alternatively, predefined dimensions or shapes or surfaces can be selected based on the imaging data to achieve an optimal fit with the patient's articular surface(s) intraoperatively.

2. Other Applications of Patient-Specific Tools, Devices and Methods

In some embodiments, the methods and devices described herein can be used to locate and harvest grafts for semitendinosus and/or gracilis autograft (hamstrings). The site of such grafts can be difficult to locate precisely, and the difficulty can cause some surgeons to avoid the procedure altogether. The site is generally approximately 5 cm distal from the anterior tibial plateau eminence. A surgical device based on patient-specific information can provide the precise location of such a graft and improve the ability of surgeons to perform such procedures as well as the reliability of the procedure itself and the associated patient outcome.

In some embodiments, devices and techniques can be employed to determine the size of grafts needed for ligament repair. For example, patient-specific information can be employed to determine the size of the native cruciate ligament in the knee, or other ligaments. Even if torn or stretched, the size of the ligament can be estimated from the joint spacing, bone structure, and the ligament itself either manually or, alternatively, partially or entirely with the assistance of automated software. For this purpose, kinematic simulations can be employed or integrated with the imaging data. These simulations can, for example, determine graft length for different flexion and extension angles. Moreover, different insertions and origins can be determined and optimized based on available grafts and graft lengths.

In some embodiments, devices and methods can be employed to observe the size of hamstring tissue available to serve as a graft for the repair of the ACL, PCL or other ligaments. Such embodiments are advantageous in part, because they help ensure that the size of the graft, e.g., length and/or diameter.

In some embodiments, patient-specific surgical instruments or other patient-specific devices can be placed and or used via a robotic device or other similar devices. Patient specific surgical instruments can be attached to a limb or a joint surface substantially conforming to the patient's anatomy. The patient specific surgical instrument can then be linked to a robot, e.g., by mechanical, magnetic, electronic or wireless means. The position of the patient specific surgical instrument can help cross-reference the location of the extremity or the articular or other patient geometry and the robot or any surgical instruments attached to the robot or operated via the robot in a fast and time efficient manner. Patient specific surgical instruments can also be used for cross-referencing the anatomy for surgical navigation systems. In this manner, time-consuming steps of registering a robot or navigation system relative to the patient's anatomy can be greatly accelerated, thereby reducing the time needed for the procedure.

In some embodiments, sensors can be placed on surgical guides and other instruments, for example, to assist with proper registration of the guides to an articular surface or otherwise assist in steps of the procedure. Similarly, sensors can be used in conjunction with an endoscope or arthroscopic portal to provide information with respect to the placement and function of the surgical guide or other device. Sensors can be optical or radiofrequency based. Sensors can be wireless. Sensors can also include pressure probes and enable pressure measurements.

In some embodiments, the surgical guide may include an aiming device or other device to assist in the placement of the device or in other steps of the procedure. Such a device can, for example, assist with the placement of the distal and proximal tunnels of an ACL or PCL reconstruction.

In some embodiments, a patient-specific template can match or register a bone characteristic or marker, for example, the notch of the knee joint or an osteophyte, to assist with proper placement and alignment.

In some embodiments, the direction vectors of one or more bone tunnels can be positioned to facilitate proper alignment and placement of the tunnels. For example, in an ACL reconstruction, a tibial tunnel may be aligned towards the femur using a medial approach in which the tibial tunnel is aligned with a lateral directional component relative to the notch. This may improve resistance and/or rotational stability. This also may allow a more circular aperture with less angle at the opening of the tunnel on the articular surface. Similarly, in still other embodiments, the vectors of the tunnels can be chosen to navigate around structures, for example, deformities in the bone, hardware from previous surgeries, arthroplasty implants, devices implanted at the time of the ligament procedure.

In some embodiments, a patient-specific device is placed posteriorly to protect the guide pin that the drill passes over during the surgical procedure.

In some embodiments, the alignment of the tunnels can be established by taking the joint through flexion and extension and ensuring that the template is registered and aligned in flexion, extension, and/or in interim positions. This registration and/or alignment can occur on one articular surface or by referencing both articular surfaces.

In some embodiments, the instrumentation for placement can be virtual. For example, in one such embodiment, a video feed from an endoscope inserted into the surgical area, or a video camera or other sensor device can otherwise placed at the surgical site during a procedure. In the case where an endoscope is used, the video feed is processed to provide the surgeon with the video information normally viewed, and is additionally processed in conjunction with imaging data (such as CT or MRI data) created prior to the surgery. A computer or similar device processes the information and compares the view from the endoscope to the imaging data to determine the proper placement of the associated tunnel or otherwise guides other and additional steps during the procedure. For example, in some embodiments, a visual mark can be displayed showing the proper placement of a tunnel and/or an instrumentation device. In other embodiments, further sensors can be included, for example, on a cutting or drilling tool, to virtually determine and/or verify the proper orientation of the tunnel.

Additional principles and concepts related broadly to patients-specific surgical devices and methods, including, without limitation, to the surgical tools described above for ligament repair, are discussed in greater detail in the following sections.

3. Assessment of Patient-Specific Anatomy 3.1 Imaging Techniques

As can be appreciated by those of skill in the art, the practice of the embodiments that employ imaging techniques preferably employ conventional methods of x-ray imaging and processing, x-ray tomosynthesis, ultrasound including A-scan, B-scan and C-scan, computed tomography (CT scan), magnetic resonance imaging (MRI), optical coherence tomography, single photon emission tomography (SPECT) and positron emission tomography (PET) within the skill of the art. However, other imaging techniques are possible. Imaging techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher; and Dental Radiology: Understanding the X-Ray Image, editor Laetitia Brocklebank 1997, Oxford University Press publisher. See also, The Essential Physics of Medical Imaging ($2^{nd}$ Ed.), Jerrold T. Bushberg, et al.

As can be appreciated by those of skill in the art, imaging techniques suitable for measuring thickness and/or curvature (e.g., of cartilage and/or bone) or size of areas of diseased cartilage or cartilage loss include the use of x-rays, magnetic resonance imaging (MRI), computed tomography scanning (CT, also known as computerized axial tomography or CAT), optical coherence tomography, ultrasound imaging techniques, and optical imaging techniques. (See, also, International Patent Publication WO 02/22014 to Alexander et al., published Mar. 21, 2002; U.S. Pat. No. 6,373,250 to Tsoref et al., issued Apr. 16, 2002; and Vandeberg et al. (2002) *Radiology* 222:430-436). Contrast or other enhancing agents can be employed using any route of administration, e.g., intravenous, intra-articular, and/or other route of administration.

3.2 Intraoperative Measurements

Alternatively, or in addition to, non-invasive imaging techniques described above, measurements of the size of an anatomical area, for example, an area of diseased cartilage or an area of cartilage loss, measurements of cartilage thickness and/or curvature of cartilage or bone can be obtained intraoperatively during arthroscopy or open arthrotomy. Intraoperative measurements can, but need not, involve actual contact with one or more areas of the articular surfaces.

Devices suitable for obtaining intraoperative measurements of cartilage or bone or other articular structures, and to generate a topographical map of the surface include but are not limited to, Placido disks, optical measurements tools and device, optical imaging tools and devices, and laser interferometers, and/or deformable materials or devices. (See, for example, U.S. Pat. No. 6,382,028 to Wooh et al., issued May 7, 2002; U.S. Pat. No. 6,057,927 to Levesque et al., issued May 2, 2000; U.S. Pat. No. 5,523,843 to Yamane et al. issued Jun. 4, 1996; U.S. Pat. No. 5,847,804 to Sarver et al. issued Dec. 8, 1998; and U.S. Pat. No. 5,684,562 to Fujieda, issued Nov. 4, 1997).

4. Design and Manufacturing of Patient-Specific Devices

Ligaments, menisci and other articular structures can be displayed in 2-D and 3-D. For a description of various parametric surface representations see, for example Foley, J. D. et al., Computer Graphics: Principles and Practice in C; Addison-Wesley, $2^{nd}$ edition, 1995).

The 2-D or 3-D representations of the cartilage and/or subchondral bone and other anatomic structures and the articular repair system can be merged into a common coordinate system. The articular repair system, including surgical tools and instruments, molds, in situ repair systems, and/or other components, can then be placed at the desired implantation site. The representations of the cartilage, subchondral bone, ligaments, menisci and other anatomic structures and the articular repair system are rendered into a 2-D or 3-D image, for example application programming interfaces (APIs) OpenGL® (standard library of advanced 3-D graphics functions developed by SGI, Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 2-D or 3-D image can be rendered or displayed showing the cartilage, subchondral bone, ligaments, menisci or other anatomic objects, and the articular repair system from varying angles, e.g. by rotating or moving them interactively or non-interactively, in real-time or non-real-time.

5. Other Patient-Specific Surgical Tools

Surgical assistance, both for the use of patient-specific implants and procedures as well as other devices and procedures, can be provided by using a device applied to the outer surface of the articular cartilage or the bone, including the subchondral bone, in order to match the alignment of the articular repair system and the recipient site or the joint. The device can be round, circular, oval, ellipsoid, curved or irregular in shape. The shape can be selected or adjusted to match or enclose an area of diseased cartilage or an area slightly larger than the area of diseased cartilage or substantially larger than the diseased cartilage. The area can encompass the entire articular surface or the weight bearing surface. Such devices are typically preferred when replacement of a majority or an entire articular surface is contemplated.

Mechanical devices can be used for surgical assistance (e.g., surgical tools), for example using gels, molds, plastics or metal. One or more electronic images or intraoperative measurements can be obtained providing object coordinates that define the articular and/or bone surface and shape. These objects' coordinates can be utilized to either shape the device, e.g. using a CAD/CAM technique, to conform to (i.e., substantially match or register) a patient's articular anatomy or, alternatively, to select a typically pre-made device that has a good fit with a patient's articular anatomy. The device can have a surface and shape that substantially matches all or portions of the articular cartilage, subchondral bone and/or other bone surface and shape. The device can include, without limitation, one or more cut planes, apertures, slots and/or holes to accommodate surgical instruments such as drills, reamers, curettes, k-wires, screws and saws.

The mold may be designed to rest on bone or cartilage outside the area to be worked on, e.g. cut, drilled, and/or worked on in other ways. In this manner, multiple surgical steps can be performed using the same mold. For example, in the knee, the mold may be stabilized against portions of the intercondylar notch, which can be selected external to areas to be removed for total knee arthroplasty or other procedures. The mold may be affixed to the underlying bone, for example with pins or drills, and/or other devices.

In additional embodiments, the mold may rest on the articular cartilage. The mold may rest on the subchondral bone or on structures external to the articular surface that are within the joint space or on structures external to the joint space. If the mold is designed to rest on the cartilage, an imaging test demonstrating the articular cartilage can be used in one embodiment. This can, for example, include ultrasound, spiral CT arthrography, MRI using, for example, cartilage displaying pulse sequences, or MRI arthrography. In another embodiment, an imaging test demonstrating the subchondral bone, e.g. CT or spiral CT, can be used and a standard cartilage thickness can be added to the scan. The standard cartilage thickness can be derived, for example, using an anatomic reference database, age, gender, and race matching, age adjustments and any method known in the art or developed in the future for deriving estimates of cartilage thickness. The standard cartilage thickness may, in some embodiments, be uniform across one or more articular surfaces or it can change across the articular surface.

The mold may be adapted to rest substantially on subchondral bone. In this case, residual cartilage can create some offset and inaccurate result with resultant inaccuracy in surgical cuts, drilling and the like. In one embodiment, the residual cartilage is removed in a first step in areas where the mold is designed to contact the bone and the subchondral bone is exposed. In a second step, the mold is then placed on the subchondral bone.

With advanced osteoarthritis, significant articular deformity can result. The articular surface(s) can become flattened. There can be cyst formation or osteophyte formation. "Tram track" like structures can form on the articular surface. In some embodiments, osteophytes or other deformities may be removed by the computer software prior to generation of the mold. The software can automatically, semi-automatically or manually with input from the user simulate surgical removal of the osteophytes or other deformities, and predict the resulting shape of the joint and the associated surfaces. The mold can then be designed based on the predicted shape. Intraoperatively, these osteophytes or other deformities can then also optionally be removed prior to placing the mold and performing the procedure. Alternatively, the mold can be designed to avoid such deformities. For example, the mold may only be in contact with points on the articular surface or external to the articular surface that are not affected or involved by osteophytes. The mold can rest on the articular surface or external to the articular surface on three or more points or small surfaces with the body of the mold elevated or detached from the articular surface so that the accuracy of its position cannot be affected by osteophytes or other articular deformities. The mold can rest on one or more tibial spines or portions of the tibial spines. Alternatively, all or portions of the mold may be designed to rest on osteophytes or other excrescences or pathological changes.

The template may be a mold that can be made of a plastic or polymer. The mold may be produced by rapid prototyping technology, in which successive layers of plastic are laid down, as know in the art. In other embodiments, the template or portions of the template can be made of metal. The mold can be milled or made using laser based manufacturing techniques.

The template may be casted using rapid prototyping and, for example, lost wax technique. It may also be milled. For example, a preformed mold with a generic shape can be used at the outset, which can then be milled to the patient specific dimensions. The milling may only occur on one surface of the mold, preferably the surface that faces the articular surface. Milling and rapid prototyping techniques may be combined.

Curable materials may be used which can be poured into forms that are, for example, generated using rapid prototyping. For example, liquid metal may be used. Cured materials may optionally be milled or the surface can be further refined using other techniques.

Metal inserts may be applied to plastic components. For example, a plastic mold may have at least one guide aperture to accept a reaming device or a saw. A metal insert may be used to provide a hard wall to accept the reamer or saw. Using this or similar designs can be useful to avoid the accumulation of plastic or other debris in the joint when the saw or other surgical instruments may get in contact with the mold. Other hard materials can be used to serve as inserts. These can also include, for example, hard plastics or ceramics.

In another embodiment, the mold does not have metallic inserts to accept a reaming device or saw. The metal inserts or guides may be part of an attached device that is typically in contact with the mold. A metallic drill guide or a metallic saw guide may thus, for example, have metallic or hard extenders that reach through the mold thereby, for example, also stabilizing any devices applied to the mold against the physical body of the mold.

The template may not only be used for assisting the surgical technique and guiding the placement and direction of surgical instruments. In addition, the templates can be utilized for guiding the placement of a graft, implant or implant components.

One or more templates can be used during the surgery. It is also possible to make templates that are designed to fit to a bone or portions of a joint after the surgeon has already performed selected surgical procedures, such as cutting, reaming, drilling, and/or other procedures. The template can account for the shape of the bone or the joint resulting from these procedures.

Information about other joints or axis and alignment information of a joint or extremity can be included when selecting the position of the, without limitation, cut planes, apertures, slots or holes on the template, in accordance with some embodiments. The biomechanical and/or anatomic axes may be derived using above-described imaging techniques including, without limitation, a standard radiograph, including a load bearing radiograph, for example an upright knee x-ray or a whole leg length film (e.g., hip to foot). These radiographs may be acquired in different projections, for example anteroposterior, posteroanterior, lateral, oblique, and/or other projections. The biomechanical and anatomic axes may also be derived using other imaging modalities such as CT scan or MRI scan, a CT scout scan or MRI localized scans through portions or all of the extremity, either alone or in combination, as described in above embodiments. For example, when total or partial knee arthroplasty is contemplated, a spiral CT scan may be obtained through the knee joint. The spiral CT scan through the knee joint serves as the basis for generating the negative contour template(s)/mold(s) that are affixed to portions or all of the knee joint. Additional CT or MRI scans may be obtained through the hip and ankle joint. These may be used to define the centroids or centerpoints in each joint or other anatomic landmarks, for example, and then to derive the biomechanical and other axes.

In another embodiment, the biomechanical axis may be established using non-image based approaches including traditional surgical instruments and measurement tools such as intramedullary rods, alignment guides and also surgical navigation. For example, in a knee joint, optical or radiofrequency markers can be attached to the extremity. The lower limb may then be rotated around the hip joint and the position of the markers can be recorded for different limb positions. The center of the rotation can determine the center of the femoral head. Similar reference points may be determined in the ankle joint and/or other locations. The position of the templates or, more typically, the position of surgical instruments relative to the templates may then be optimized for a given biomechanical load pattern, for example in varus or valgus alignment. Thus, by performing these measurements pre- or intraoperatively, the position of the surgical instruments may be optimized relative to the molds and the cuts can be placed to correct underlying axis errors such as varus or valgus malalignment or ante- or retroversion.

Upon imaging, a physical template can be generated. The template can be used to perform image guided surgical procedures such as partial or complete joint replacement, articular resurfacing, or ligament repair. The template may include reference points or opening or apertures for surgical instruments such as drills, saws, burrs and the like.

In order to derive the preferred orientation of drill holes, cut planes, saw planes and the like, openings or receptacles in said template or attachments can be adjusted to account for at least one axis. The axis can be anatomic or biomechanical, for example, for a knee joint, a hip joint, an ankle joint, a shoulder joint or an elbow joint.

In one embodiment, only a single axis is used for placing and optimizing such drill holes, saw planes, cut planes, and or other surgical interventions. This axis may be, for example, an anatomical or biomechanical axis. In some embodiments, a combination of axis and/or planes can be used for optimizing the placement of the drill holes, saw planes, cut planes or other surgical interventions. For example, two axes (e.g., one anatomical and one biomechanical) can be factored into the position, shape or orientation of the 3D guided template and related attachments or linkages. For example, two axes, (e.g., one anatomical and biomechanical) and one plane (e.g., the top plane defined by the tibial plateau), can be used. Alternatively, two or more planes can be used (e.g., a coronal and a sagittal plane), as defined by the image or by the patients anatomy.

Angle and distance measurements and surface topography measurements may be performed in these one or more, preferably two or more, preferably three or more multiple planes, as desired. These angle measurements can, for example, yield information on varus or valgus deformity, flexion or extension deficit, hyper or hypo-flexion or hyper- or hypo-extension, abduction, adduction, internal or external rotation deficit, or hyper-or hypo-abduction, hyper- or hypo-adduction, hyper- or hypo-internal or external rotation.

Single or multi-axis line or plane measurements can then be utilized to determine preferred angles of correction, e.g., by adjusting surgical cut or saw planes or other surgical interventions. Typically, two axis corrections can be preferred over a single axis correction, a two plane correction are preferred over a single plane correction and so forth.

In accordance with some embodiments, more than one drilling, cut, boring and/or reaming or other surgical intervention is performed for a particular treatment such as the placement of a joint resurfacing or replacing implant, or components thereof. These two or more surgical interventions (e.g., drilling, cutting, reaming, sawing) are made in relationship to a biomechanical axis, and/or an anatomical axis and/or an implant axis. The guidance template or attachments or linkages thereto include two or more openings, guides, apertures or reference planes to make at least two or more drillings, reamings, borings, sawings or cuts in relationship to a biomechanical axis, an anatomical axis, an implant axis or other axis derived therefrom or related thereto.

In both single-use and re-useable embodiments, the tool can be designed so that the instrument controls the depth and/or direction of the drill, i.e., the drill cannot go any deeper into the tissue than the instrument allows.

The foregoing description of embodiments has been provided for the purposes of illustration and description. It is not intended to be exhaustive or to limit the invention to the precise forms disclosed. Many modifications to, variations of, combinations of, and additions to the embodiments described herein are readily apparent to those skilled in the art, and many additional embodiments are possible. The generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

What is claimed is:

1. A method for making a surgical instrument system for ligament repair, the method comprising:
    obtaining electronic image data of at least one surface associated with a ligament of a patient;
    determining a tunnel site for a ligament graft based, at least in part, on the electronic image data; and
    creating a first template based, at least in part, on the electronic image data, the template having at least one contact surface that conforms with at least a portion of the at least one surface associated with the ligament of the patient, the template including at least one guide for directing movement of a surgical instrument involved with the ligament repair, wherein the at least one guide is configured based, at least in part, on the tunnel site.

2. The method according to claim 1, wherein the ligament is an anterior cruciate ligament.

3. The method according to claim 1, wherein the ligament is a posterior cruciate ligament.

4. The method according to claim 1, wherein determining the tunnel site includes identifying an origin of the ligament on a first articular surface, and an insertion position onto a second articular surface opposing the first articular surface.

5. The method according to claim 1, wherein determining the tunnel site includes identifying at least one of a bony landmark and a remainder of a ligament based on the image data.

6. The method according to claim 1, wherein the at least one surface is one of adjacent to the tunnel site and a non-weight bearing surface.

7. The method according to claim 1, wherein the first template includes a drill guide aperture.

8. The method according to claim 7, wherein at least one of the shape, position and orientation of the drill guide aperture on the first template is based, at least in part, on a distance of the tunnel site to adjacent cortical bone.

9. The method according to claim 8, wherein the drill guide aperture includes a stop, such that a desired drill depth is obtained.

10. The method according to claim 1, wherein the electronic image data is obtained in at least one of joint flexion, joint extension, joint abduction, joint adduction, and joint rotation.

11. The method according to claim 1, further comprising:
    identifying a graft harvest site based on the image data; and
    configuring the first template to guide harvesting of at least one of ligament and bone from the graft harvest site.

12. The method according to claim 1, further comprising:
    creating a second template configured to cross-reference to the first template to align a position of the second template on a second surface associated with the ligament, the second template including at least one guide configured to direct
    movement of the surgical instrument using the at least one guide of the second template relative to said guide.

13. The method according to claim 12, wherein the at least one and second surfaces are opposing articular surfaces.

14. The method according to claim 13, wherein the at least one surface is a femoral surface and the second surface is a tibial surface.

15. The method according to claim 1, wherein the first template includes a tissue retractor.

16. The method according to claim 15, wherein the tissue retractor is one of a flange and an extender.

17. The method according to claim 1, wherein the first template is configured for use in at least one of a single bundle and a double bundle ligament reconstruction.

18. A method for making a surgical instrument system for repairing an anterior cruciate ligament (ACL) of a patient's knee joint, the method comprising:
    obtaining electronic image data of at least one surface associated with the ACL;
    determining a femoral tunnel site and a tibial tunnel site for a ligament graft based, at least in part, on the electronic image data; and
    creating a first template based, at least in part, on the electronic image data, the first template having at least one contact surface that conforms with at least a portion of the at least one surface associated with the ACL, the first template including at least one guide for directing movement of a surgical instrument involved with the ACL repair, wherein the at least one guide is configured based, at least in part, on the femoral and tibial tunnel sites.

19. The method of claim 18, wherein the femoral or tibial tunnel site is optimized for a knee pose angle.

20. The method of claim 18, wherein the femoral or tibial tunnel site is optimized for a range of motion of the patient's knee joint.

* * * * *